(12) United States Patent
Hashimoto et al.

(10) Patent No.: US 10,122,975 B2
(45) Date of Patent: Nov. 6, 2018

(54) ENDOSCOPE AND ENDOSCOPE SYSTEM

(71) Applicant: PANASONIC INTELLECTUAL PROPERTY MANAGEMENT CO., LTD., Osaka (JP)

(72) Inventors: Yota Hashimoto, Fukuoka (JP); Haruyasu Katahira, Fukuoka (JP); Yuuichi Takenaga, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 30 days.

(21) Appl. No.: 15/480,849

(22) Filed: Apr. 6, 2017

(65) Prior Publication Data

US 2017/0339377 A1 Nov. 23, 2017

(30) Foreign Application Priority Data

May 19, 2016 (JP) .................................. 2016-100738
Sep. 21, 2016 (JP) .................................. 2016-184797

(51) Int. Cl.
*A61B 1/00* (2006.01)
*H04N 9/097* (2006.01)
(Continued)

(52) U.S. Cl.
CPC ......... *H04N 9/097* (2013.01); *A61B 1/00096* (2013.01); *A61B 1/00186* (2013.01);
(Continued)

(58) Field of Classification Search
CPC .. H04N 9/64; A61B 1/00009; A61B 1/00186; G02B 27/103
(Continued)

(56) References Cited

U.S. PATENT DOCUMENTS 5,777,674 A 7/1998 Ohmuro
5,910,816 A * 6/1999 Fontenot ............... A61B 5/0059
348/162

(Continued)

FOREIGN PATENT DOCUMENTS

DE 102009024943 A1 12/2010
EP 3072437 A1 9/2016
(Continued)

*Primary Examiner* — Jeffery A Williams
(74) *Attorney, Agent, or Firm* — Greenblum & Bernstein, P.L.C.

(57) ABSTRACT

An endoscope includes a four color separation prism having a first color separation prism, a second color separation prism, a third color separation prism, and a fourth color separation prism which respectively separate light incident from an affected area into a blue, red and green color components, and an IR component, first, second, third and fourth color image sensors, and a signal output. The first color separation prism, the second color separation prism, the third color separation prism, and the fourth color separation prism are sequentially disposed from an object side when receiving the light incident from the affected area. The first color image sensor is disposed opposite to the second color image sensor and the third color image sensor across an incident ray which is incident vertically to an object side incident surface of the first color separation prism.

10 Claims, 20 Drawing Sheets

(51) Int. Cl.
    *A61B 1/04*     (2006.01)
    *A61B 1/05*     (2006.01)
    *A61B 5/00*     (2006.01)
    *G02B 23/04*     (2006.01)
    *G02B 23/24*     (2006.01)
    *G02B 27/10*     (2006.01)
    *G02B 27/14*     (2006.01)
    *H04N 5/225*     (2006.01)
    *H04N 5/33*     (2006.01)
    *H04N 9/04*     (2006.01)

(52) U.S. Cl.
CPC .............. *A61B 1/043* (2013.01); *A61B 1/051* (2013.01); *A61B 5/0071* (2013.01); *A61B 5/0086* (2013.01); *G02B 23/04* (2013.01); *G02B 23/2453* (2013.01); *G02B 27/1013* (2013.01); *G02B 27/143* (2013.01); *G02B 27/145* (2013.01); *H04N 5/2254* (2013.01); *H04N 5/332* (2013.01); *H04N 9/045* (2013.01); *A61B 5/0077* (2013.01); *A61B 5/6847* (2013.01); *A61B 2505/05* (2013.01); *A61B 2562/0233* (2013.01); *A61B 2576/00* (2013.01); *H04N 2005/2255* (2013.01); *H04N 2209/048* (2013.01)

(58) Field of Classification Search
USPC .......................................................... 348/71
See application file for complete search history.

(56) References Cited

U.S. PATENT DOCUMENTS

| | | |
|---|---|---|
| 2012/0050877 A1 | 3/2012 | Saita |
| 2012/0268573 A1 | 10/2012 | Schonborn et al. |
| 2015/0256733 A1 | 9/2015 | Kanamori |

FOREIGN PATENT DOCUMENTS

| | | |
|---|---|---|
| JP | 7-281012 A | 10/1995 |
| JP | 9-11445 A | 1/1997 |
| JP | 2012-047805 A | 3/2012 |
| JP | 2013116353 A | 6/2013 |
| JP | 2015-180864 A | 10/2015 |
| WO | 2009/117483 A1 | 9/2009 |

\* cited by examiner

ENDOSCOPE AND ENDOSCOPE SYSTEM

BACKGROUND

1. Technical Field

The present disclosure relates to an endoscope and an endoscope system.

2. Description of the Related Art

In the related art, an endoscope system using a three color separation prism is known. For example, Japanese Patent Unexamined Publication No. 2013-116357 discloses the endoscope system. The endoscope system acquires a captured color image on which a specific area in a body is expressed in combination with three colors of R (red color), G (green color), and B (blue color), and performs image processing on the captured image in order to emphasize a designated wavelength component.

According to the endoscope system disclosed in Japanese Patent Unexamined Publication No. 2013-116357, if an IR light (infrared light) component is added to the image in addition to the three colors of RGB, the image captured by an endoscope shows insufficient image quality.

SUMMARY

The present disclosure is made in view of the above-described circumstances, and aims to provide an endoscope and an endoscope system which can improve image quality by adding an infrared light component to an image.

An endoscope according to the present disclosure includes a four color separation prism that includes a first color separation prism, a second color separation prism, a third color separation prism, and a fourth color separation prism which respectively separate light incident from an affected area into a first color component, a second color component, a third color component, and a fourth color component which are any one of a blue color component, a red color component, a green color component, and an IR component, a first color image sensor that is installed in the first color separation prism, and that converts the separated first color component into an electric signal, a second color image sensor that is installed in the second color separation prism, and that converts the separated second color component into an electric signal, a third color image sensor that is installed in the third color separation prism, and that converts the separated third color component into an electric signal, a fourth color image sensor that is installed in the fourth color separation prism, and that converts the separated fourth color component into an electric signal, and a signal output that outputs a color image signal and an IR signal from the respectively converted electric signals. The first color separation prism, the second color separation prism, the third color separation prism, and the fourth color separation prism are sequentially disposed from an object side when receiving the light incident from the affected area. The first color image sensor is disposed opposite to the second color image sensor and the third color image sensor across an incident ray which is incident vertically to an object side incident surface of the first color separation prism.

According to the present disclosure, it is possible to improve image quality of an image captured by an endoscope by adding an infrared light component to the captured image.

DETAILED DESCRIPTION

Background of Exemplary Embodiment in Present Disclosure

In surgery using an endoscope, an indocyamine green (ICG) which is a fluorescent substance is administered into a body, and near infrared light is emitted to an area such as an excessively accumulated tumor (affected area). The affected area is lightened so as to image an area including the affected area in some cases. If the ICG is excited by the near infrared light (for example, peak wavelength of 805 nm, 750 to 810 nm), the ICG is a substance which fluoresces using the near infrared light having a longer wavelength (for example, peak wavelength of 835 nm).

In a case where a single board-type camera having one image sensor acquires an image of the affected area by receiving light containing an IR component, a filter for a red color (R) component, a green color (G) component, a blue color (B) component, and the IR component which are divided into four is disposed on an incident surface of the image sensor. Therefore, if a user tries to obtain desired color reproducibility and resolution, a size of the image sensor has to increase. Consequently, the single board-type camera is less likely to be applied to the endoscope.

Figure 13:
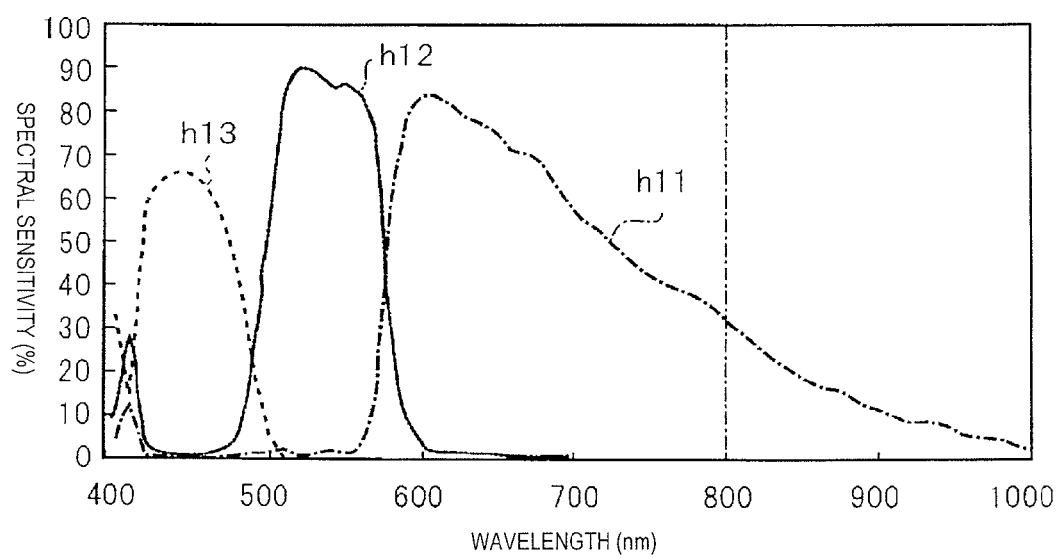
FIG. 13 is a graph illustrating spectral sensitivity of a three color separation prism according to a comparative example.

As illustrated in the endoscope system disclosed in Japanese Patent Unexamined Publication No. 2013-116357, in a case where a triple board-type camera using a three color separation prism acquires an image of the affected area by receiving the light containing the IR component, signal strength of the IR component (for example, light having a wavelength of 800 nm or greater) is weak as illustrated in FIG. 13.

FIG. 13 is a graph illustrating spectral sensitivity of the triple board-type camera according to a comparative example. In FIG. 13, a vertical axis represents the spectral sensitivity, and a horizontal axis represents a wavelength. The spectral sensitivity corresponds to a ratio between a light quantity of light incident on each prism for the R-component, the G-component, and the B-component, and a light quantity detected by an imaging element corresponding to each prism. Waveform h11 represents the spectral sensitivity of the light having the R-component. Waveform h12 represents the spectral sensitivity of the light having the G-component. Waveform h13 represents the spectral sensitivity of the light having the B-component. Waveform h11 also includes represents the spectral sensitivity of the light having the IR component.

As illustrated in FIG. 13, the image sensor which receives the light having the R-component (refer to waveform h11) can acquire the light having the IR component. In FIG. 13, the spectral sensitivity of the IR component (for example, component having a wavelength of 800 nm or greater) is lower than the spectral sensitivity of the light having the R-component, the G-component, and the B-component. If the signal strength of the IR component is weak, an image (IR image) obtained by the IR component is unclear. Accordingly, it is preferable to increase the signal strength of the IR component so that the image (IR image) obtained by the IR component becomes clearer.

On the other hand, if the endoscope system disclosed in Japanese Patent Unexamined Publication No. 2013-116357 amplifies the IR component in order to increase the signal strength of the IR component, the image blurs or noise is emphasized on the image. Consequently, image quality of the IR image becomes poor. Therefore, a desired area (affected area) containing the IR component is less likely to be observed from the image obtained by the amplified IR component.

In a case of using the triple board-type camera, a blue color separation prism is normally disposed in the three color separation prism, as a prism on an object side on the light is incident. The reason is as follows. The blue color component has a shorter wavelength than that of the red color component and the green color component. As the wavelength becomes shorter, the blue color component is less likely to receive the influence of polarized light.

In a case where a four color separation prism is disposed in the endoscope, the endoscope has a limited space for disposing the four color separation prism. Accordingly, it is preferable to devise a method of disposing a prism for each color (orientation for disposing the prism or angle relating to the prism).

Hereinafter, an endoscope and an endoscope system which can improve image quality by adding an infrared light component to an image will be described.

Hereinafter, exemplary embodiments will be described in detail with proper reference to the drawings. However, in some cases, unnecessarily detailed description may be omitted. For example, in some cases, detailed description of well-known matters or repeated description of substantially the same configuration may be omitted. The reason is to avoid the following description from becoming unnecessarily redundant, and to facilitate understanding of those skilled in the art. The accompanying drawings and the following description are provided in order for those skilled in the art to fully understand the present disclosure. These are not intended to limit the gist disclosed in the scope of claims.

First Exemplary Embodiment

In a first exemplary embodiment, a quadruple board-type camera using a four color separation prism and four image sensors is disposed in a camera head of the endoscope. The four color separation prism separates light focused by a relay lens into three primary color light of R-light (R-component), G-light (G-component), and B-light (B-component), and IR light (IR component). For example, the IR component includes at least a portion of a wavelength band of 750 nm to 900 nm.

Configuration of Endoscope

Figure 1:
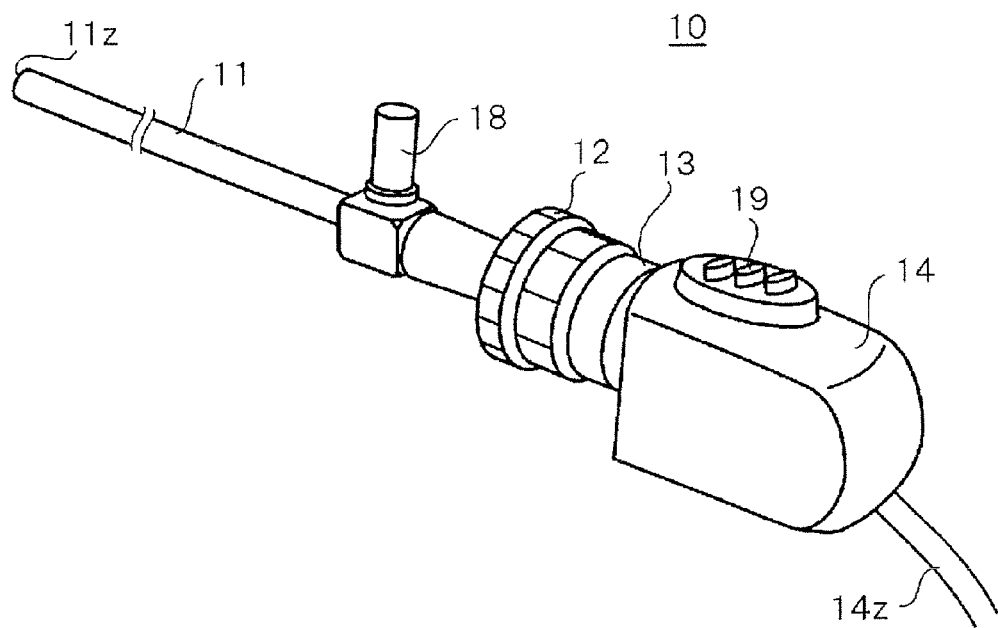
FIG. 1 is a schematic view illustrating an external configuration of an endoscope according to a first exemplary embodiment.
Figure 2:
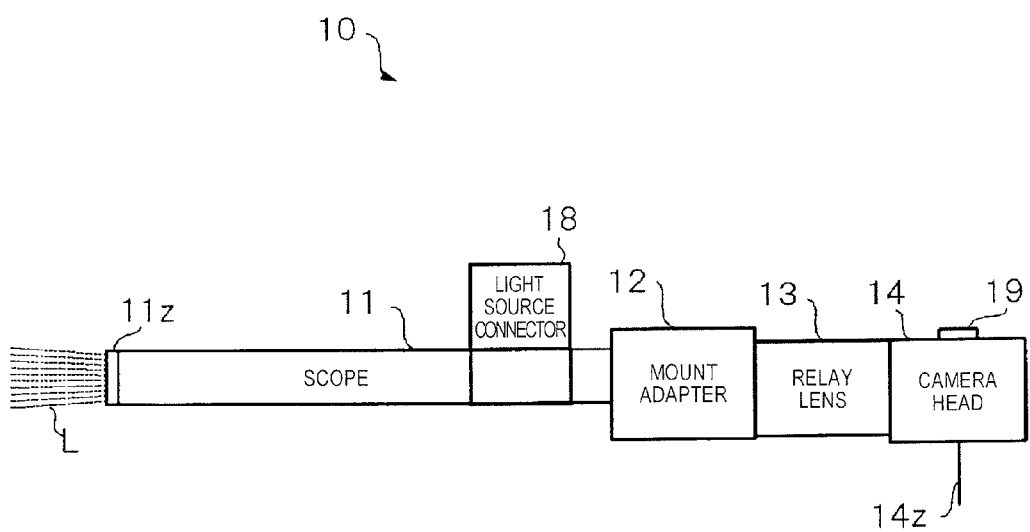
FIG. 2 is a schematic view illustrating a brief configuration of the endoscope.

FIG. 1 is a schematic view illustrating an external configuration of endoscope 10 according to the first exemplary embodiment. FIG. 2 is a schematic view illustrating a brief configuration of endoscope 10. Endoscope 10 is a medical instrument which can be handled by a user with one hand. For example, endoscope 10 is configured to include scope 11, mount adapter 12, relay lens 13, camera head 14, operation switch 19, and light source connector 18.

For example, scope 11 is a main portion of a hard endoscope, which is to be inserted into the body, and is an elongated light guide member which can guide light from a terminal end to a front end. Scope 11 has imaging window 11z in the front end, and has an optical fiber through which an optical image incident from imaging window 11z is transmitted, and an optical fiber which guides light L introduced from light source connector 18 to the front end. As imaging window 11z, optical materials such as optical glass and optical plastic are used.

Mount adapter 12 is a member for mounting scope 11 on camera head 14. Various scopes 11 can be mounted on mount adapter 12 so as to be detachable therefrom.

Light source connector 18 introduces illumination light for illuminating an area inside a body (affected area or the like) from a light source device (not illustrated). The illumination light includes visible light and IR light. The light introduced to light source connector 18 is guided to the front end of scope 11 through scope 11, and is emitted to the area inside the body (affected area or the like) from imaging window 11z. For example, the light source is an LED light source. Instead of the LED light source, the light source may be a xenon lamp or a halogen lamp.

Light source connector 18 is mounted on scope 11 via a connector between scope 11 and light source connector 18.

The connector internally has a mirror (not illustrated). The light guided from light source connector 18 is reflected on the mirror, and is emitted to the affected area after moving forward to the front end side of scope 11.

Relay lens 13 focuses an optical image transmitted through scope 11 onto an imaging surface. Relay lens 13 has one or more lenses. In accordance with an operation amount of operation switch 19, relay lens 13 may move the lens so as to perform focus adjustment and magnification adjustment.

Figure 10:
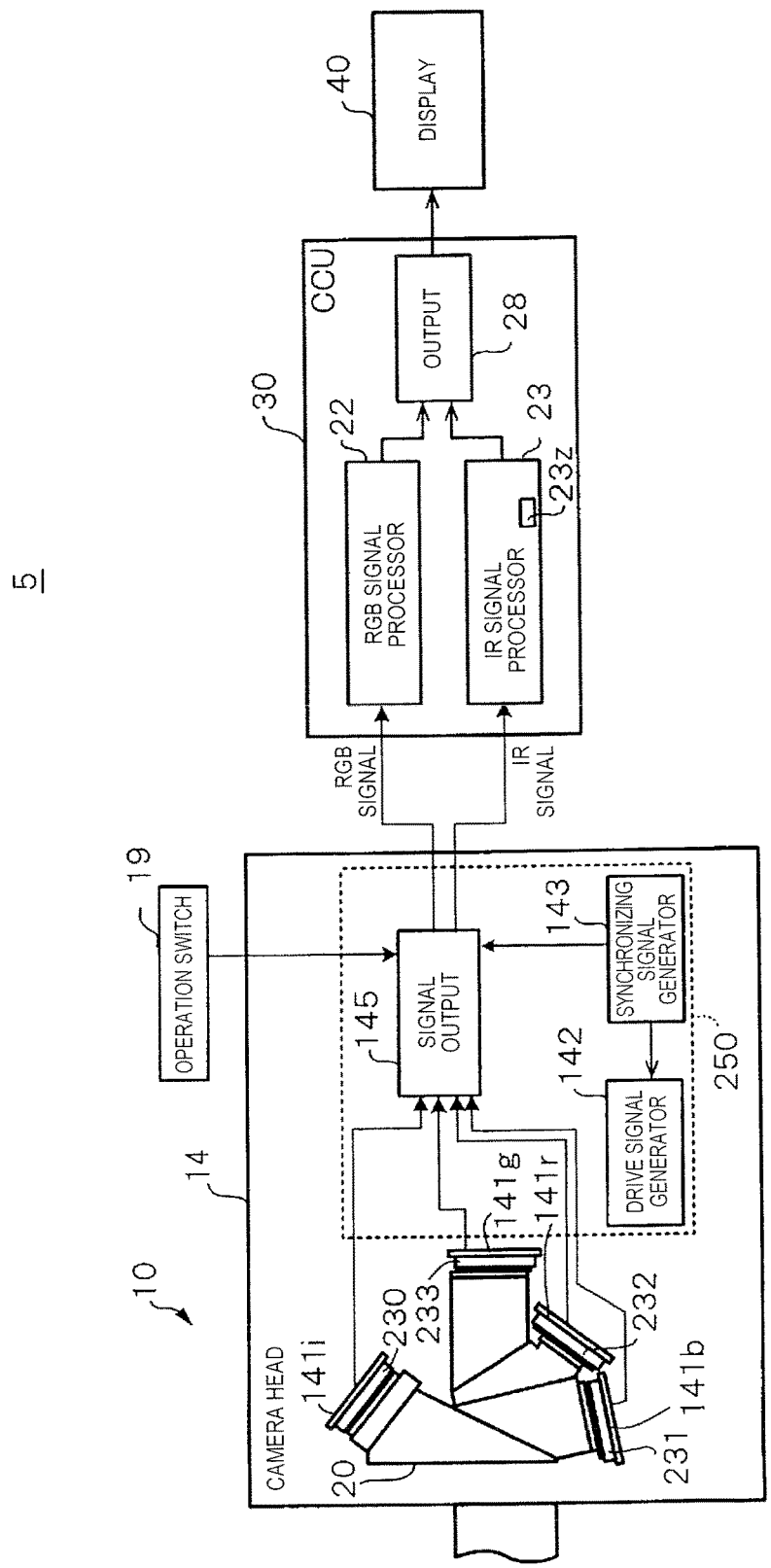
FIG. 10 is a block diagram illustrating a configuration of an endoscope system according to the first exemplary embodiment.

Camera head 14 has a housing which can be gripped by a user (for example, a doctor or an assistant) with a hand when in use (for example, during surgery), and internally has four color separation prism 20 (refer to FIGS. 5 and 6), four image sensors 230, 231, 232, and 233 (refer to FIGS. 5 and 6), and electronic board 250 (refer to FIG. 10).

Four color separation prism 20 is a quadruple board-type prism that separates light focused by relay lens 13 into three primary color light of R-light (R-component), G-light (G-component), and B-light (B-component), and IR light (IR component). Four color separation prism 20 is configured to include a light-transmitting member such as glass.

Image sensors 230 to 233 convert the optical image separated by four color separation prism 20 and formed on each imaging surface into an image signal (electric signal).

As image sensors 230 to 233, an image sensor such as a charge coupled device (CCD) or complementary metal oxide semiconductor (CMOS) is used.

Four image sensors 230 to 233 are dedicated sensors which respectively receive the light of the IR component, the B-component, the R-component, and the G-component. Therefore, unlike a single board-type camera which receives the light of the IR component, the R-component, the G-component, and the B-component by using a single image sensor, a small size image sensor can be employed as an individual image sensor. For example, an image sensor whose size is 1/2.86 inches is used.

For example, circuits including a signal output circuit for outputting a signal by using a low volt digital signal (LVDS) and a timing generator (TG) circuit (TG circuit) are mounted on electronic board 250 (simply referred to as a board) (refer to FIG. 10).

The signal output circuit outputs an RGB signal and an IR signal of an image captured by each of image sensors 230 to 233, as a pulse signal by using the low volt digital signal (LVDS). The TG circuit supplies a timing signal (synchronizing signal) to each unit inside camera head 14. The RGB signal includes at least one of the R-component, the G-component, and the B-component. Without being limited to the RGB signal, other color image signals (for example, HSV, YUV, YcCbCr, or YpbPr) may be output.

Signal cable 14z for transmitting the image signal to camera control unit (CCU) 30 (to be described later) is mounted on camera head 14.

Figure 3:
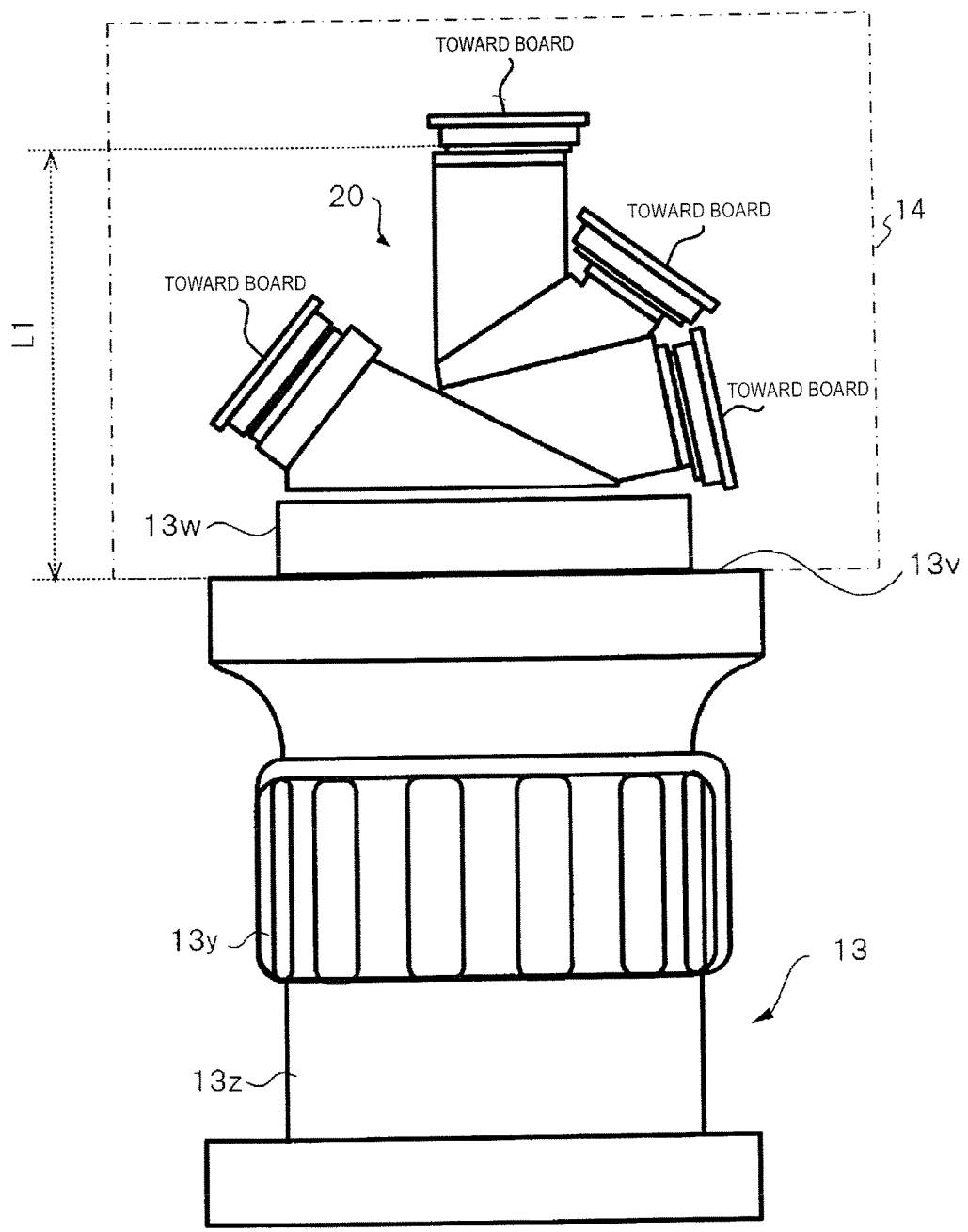
FIG. 3 is a view illustrating a camera head and a relay lens which are coupled to each other.

FIG. 3 is a view illustrating camera head 14 and relay lens 13 which are coupled to each other. An end surface of four color separation prism 20 incorporated in camera head 14 is disposed so as to face flange surface 13v of relay lens 13.

Relay lens 13 forms an image on image sensors 230 to 233 inside camera head 14 by using the light incident from a subject through scope 11 mounted on mount adapter 12.

Relay lens 13 has focus ring 13y and optical column 13z. One end portion (lower end portion in the drawing) of relay lens 13 is mounted on a mounting target portion of mount adapter 12. The other end portion (upper end portion in the drawing) of relay lens 13 has screw-thread cutter 13w having a predetermined height (for example, 4 mm).

Camera head 14 having four color separation prism 20 incorporated therein is screwed into screw-thread cutter 13w, thereby mounting relay lens 13 on camera head 14. If relay lens 13 is mounted on camera head 14 by screw-thread cutter 13w, four color separation prism 20 inside camera head 14 and the lens inside relay lens 13 face each other via a gap. The gap prevents four color separation prism 20 and relay lens 13 from coming into contact with each other.

If a distance of the gap is short, even if there is a limitation due to an optical path length of a C-mount (to be described later), four image sensors 230 to 233 are likely to be disposed outside. On the other hand, if the distance of the gap is long, since there is the limitation due to the optical path length of the C-mount, it becomes necessary to dispose four image sensors 230 to 233 inside (flange surface 13v side of relay lens 13).

For example, camera head 14 and relay lens 13 are coupled to each other in the C-mount. In the C-mount, in a state where relay lens 13 is mounted on camera head 14, a standard of an optical distance from flange surface 13v of relay lens 13 to the imaging surface of four image sensors 230 to 233 is defined as L1=17.526 mm. In a case where a quadruple board-type camera (four color separation prism 20 and image sensors 230 to 233) suitable for the optical path length of the C-mount is incorporated in camera head 14, the quadruple board-type camera is disposed so as to have this optical path length.

The light which is guided from a subject by relay lens 13 through scope 11 is focused by relay lens 13, thereby forming an image on four image sensors 230 to 233 through four color separation prism 20 inside camera head 14.

Figure 4A:
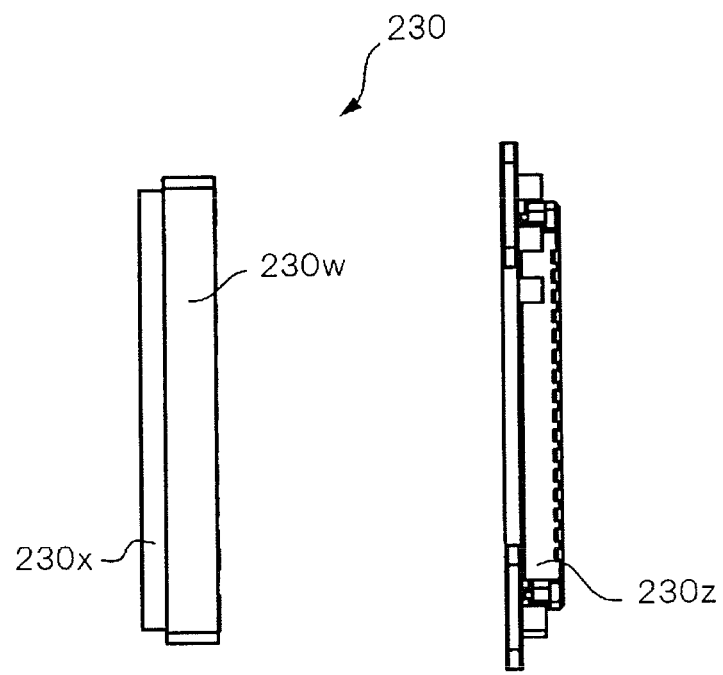
FIG. 4A is a view illustrating a configuration component of an image sensor.
Figure 4B:
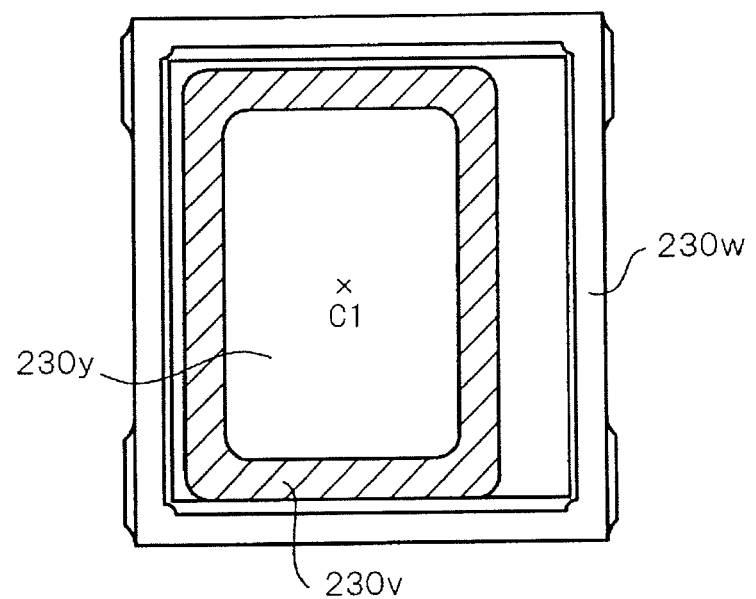
FIG. 4B is a view illustrating an external configuration of the image sensor.

FIGS. 4A and 4B are views illustrating a configuration component and an external configuration of image sensor 230. Four image sensors 230 to 233 have substantially the same specifications. Accordingly, the configuration will be described herein using IR image sensor 230.

As illustrated in FIGS. 4A and 4B, sensor element 230y is accommodated inside sensor package 230w, and is fixed thereto using adhesive 230v. Sensor package glass 230x is disposed on a front surface of sensor package 230w. Sensor element 230y receives the light transmitted through sensor package glass 230x. Sensor package 230w is mounted on sensor board 230z, and is molded as image sensor 230.

According to the present exemplary embodiment, as will be described later, image sensor 230 receives the IR light emitted from light emission surface 220c of IR separation prism (IR color separation prism) 220, and captures the IR image. Image sensors 231, 232, and 233 for capturing a visible light image also have the same structure as that of IR image sensor 230. A visible light cut filter for blocking light having the wavelength of 700 nm or smaller is disposed on the front surface of IR image sensor 230. The visible light cut filter can improve image quality of the IR image.

First Structure Example of Four Color Separation Prism

Figure 5:
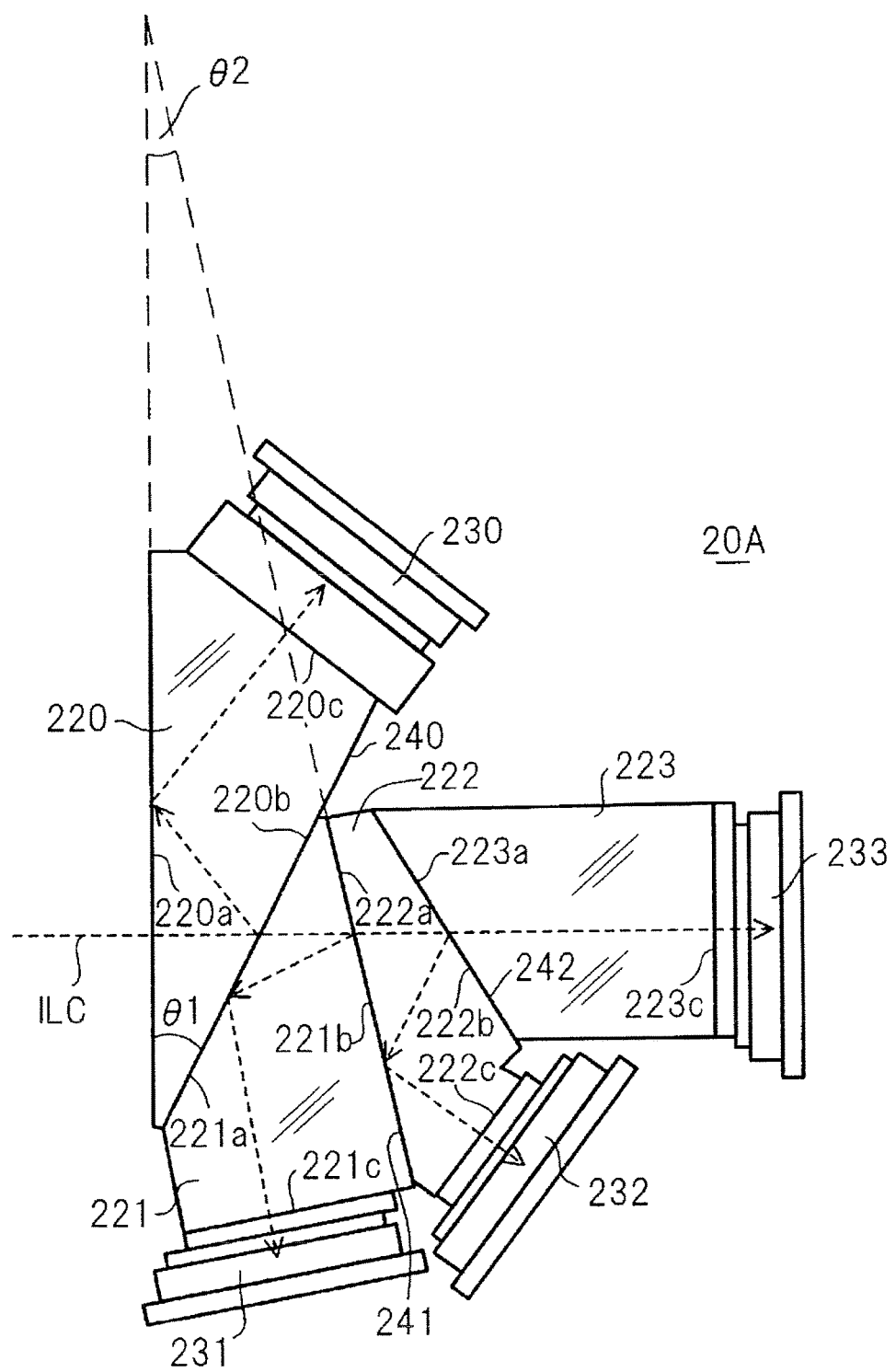
FIG. 5 is a view illustrating a first structure example of a four color separation prism.

FIG. 5 is a view illustrating a first structure example (four color separation prism 20A) of four color separation prism 20. Four color separation prism 20A separates incident light guided by relay lens 13 into the light of three primary color light of the R-component, the G-component, and the B-component, and the IR component. In four color separation prism 20A, IR separation prism 220, blue color separation prism 221, red color separation prism 222, and green color separation prism 223 are sequentially assembled in an optical axis direction. This arrangement order is an example, and other arrangement orders may be employed. In FIG. 5, as will be described later, as an angle relating to a prism, θ1>θ2 is satisfied.

As illustrated in FIG. 5, in four color separation prism 20A, angle θ1 formed between object side incident surface 220*a* of IR separation prism 220 and reflective surface 220*b* of IR separation prism 220 is formed to be greater than angle θ2 formed between an extension line of object side incident surface 220*a* of IR separation prism 220 and an extension line of reflective surface 221*b* of blue color separation prism 221. That is, θ1>θ2 is satisfied.

In other words, angle θ1 represents an angle formed between a straight line parallel to object side incident surface 220*a* of IR separation prism 220 and a straight line parallel to reflective surface 220*b*. In other words, angle θ2 represents an angle formed between the straight line parallel to object side incident surface 220*a* of IR separation prism 220 and a straight line parallel to reflective surface 221*b* of blue color separation prism 221.

IR image sensor 230 is disposed so as to face light emission surface 220*c* of IR separation prism 220. Blue color image sensor 231 is disposed so as to face light emission surface 221*c* of blue color separation prism 221. Red color image sensor 232 is disposed so as to face light emission surface 222*c* of red color separation prism 222. Green color image sensor 233 is disposed so as to face light emission surface 223*c* of green color separation prism 223.

For example, image sensors 230 to 233 are CCD or CMOS image sensors including respective pixels which are arrayed in a horizontal (H) direction and a vertical (V) direction. Image sensors 230 to 233 convert the optical image in which the light separated into each color of IR, R, G, and B forms an image on each imaging surface, into an electric signal.

In IR separation prism 220, the incident light is incident on object side incident surface 220*a* of IR separation prism 220. The light reflected on reflective surface 220*b* facing object side incident surface 220*a* is totally reflected at a boundary of object side incident surface 220*a* of IR separation prism 220, and is incident on IR image sensor 230 after being emitted from light emission surface 220*c* facing object side incident surface 220*a*. For example, IR reflective film 240 is formed on reflective surface 220*b* by vapor deposition. IR separation prism 220 causes the light of the IR component in the incident light to be reflected thereon, and causes other light (light of the B-component, the R-component, and the G-component) to be transmitted therethrough. IR image sensor 230 causes the light reflected on reflective surface 220*b* and object side incident surface 220*a* to be incident thereon, thereby receiving the light. In this way, IR separation prism 220 is molded so that the light moves forward in IR separation prism 220.

In blue color separation prism 221, the light (incident light) transmitted through IR separation prism 220 is incident on object side incident surface 221*a* of blue color separation prism 221. The light reflected on reflective surface 221*b* facing object side incident surface 221*a* is totally reflected at a boundary of object side incident surface 221*a* of blue color separation prism 221, and is incident on blue color image sensor 231 after being emitted from light emission surface 221*c* facing object side incident surface 221*a*. For example, blue light reflective film 241 is formed on reflective surface 221*b* by vapor deposition. Blue color separation prism 221 causes the light of the B-component in the incident light to be reflected thereon, and causes other light (light of the R-component and the G-component) to be transmitted therethrough. Blue color image sensor 231 causes the light reflected on reflective surface 221*b* and object side incident surface 221*a* to be incident thereon, thereby receiving the light. In this way, blue color separation prism 221 is molded so that the light moves forward in blue color separation prism 221.

In red color separation prism 222, the light (incident light) transmitted through blue color separation prism 221 is incident on object side incident surface 222*a* of red color separation prism 222. The light reflected on reflective surface 222*b* facing object side incident surface 222*a* is totally reflected at a boundary of object side incident surface 222*a* of red color separation prism 222, and is incident on red color image sensor 232 after being emitted from light emission surface 222*c* facing object side incident surface 222*a*. For example, red light reflective film 242 is formed on reflective surface 222*b* by vapor deposition. Red color separation prism 222 causes the light of the R-component in the incident light to be reflected thereon, and causes other light (light of the G-component) to be transmitted therethrough. Red color image sensor 232 causes the light reflected on reflective surface 222*b* and object side incident surface 222*a* to be incident thereon, thereby receiving the light. In this way, red color separation prism 222 is molded so that the light moves forward in red color separation prism 222.

In green color separation prism 223, the light (incident light) transmitted through red color separation prism 222 is incident on object side incident surface 223*a* of green color separation prism 223, and is incident on green color image sensor 233 after being emitted from light emission surface 223*c* facing object side incident surface 223*a*. In this way, green color separation prism 223 is molded so that the light moves forward in green color separation prism 223.

The number of light reflected times in each color separation prism is normally an even number of times (for example, twice, 0 times). The reason is that mirror image information is output from the color separation prism in a case where the number of reflected times is an odd number of times.

Consideration on Shape and Layout Relationship of Color Separation Prism

Next, a shape and a layout relationship of each color separation prism in four color separation prism 20A will be considered.

In four color separation prism 20A, IR separation prism 220 and IR image sensor 230, and blue color separation prism 221 and blue color image sensor 231 are disposed on opposite sides across incident light center line ILC. Incident light center line ILC represents an optical path of the light in a plurality of incident rays which are vertically incident on object side incident surface 220*a* of IR separation prism 220. The light is transmitted through IR separation prism 220, is transmitted through blue color separation prism 221, is transmitted through red color separation prism 222, is incident on center C1 (refer to FIG. 4B) on a light receiving surface of green color image sensor 233 facing light emission surface 233*c* of green color separation prism 223. Here, IR image sensor 230 is disposed on an upper side (refer to FIG. 5) from incident light center line ILC, and blue color image sensor 231 is disposed on a lower side (refer to FIG. 5) from incident light center line ILC.

Red color separation prism 222 and red color image sensor 232 are arranged between blue color separation prism 221 and blue color image sensor 231, and green color separation prism 223 and green color image sensor 233. Here, red color separation prism 222 and red color image sensor 232 are disposed on the lower side from incident light center line ILC, in view of a layout space inside camera head 14 (refer to FIG. 5). If the layout position of red color image sensor 232 is disposed on the upper side from incident light center line ILC, due to a limited space inside camera head 14, the layout position of red color image sensor 232 overlaps the layout position of IR image sensor 230 or the layout position of green color separation prism 223. Accordingly, it becomes difficult to physically dispose these sensors.

Since red color image sensor 232 is disposed on the lower side from incident light center line ILC, endoscope 10 enables four color separation prism 20A to be disposed inside the limited layout space. Therefore, it is possible to miniaturize camera head 14 which accommodates the four color separation prism.

In FIG. 5, IR separation prism 220 is disposed to be closest to the object side among the respective color separation prisms. That is, IR separation prism 220 is disposed closer to the object side than other color separation prisms (blue color separation prism 221, red color separation prism 222, and green color separation prism 223) when receiving the light incident from the affected area.

In this manner, IR image sensor 230 disposed to face light emission surface 220c of IR separation prism 220 can receive the IR light as much as possible. The IR light fluoresces with lower light intensity compared to the light of the B-component, the R-component, and the G-component. That is, with regard to the light incident on four color separation prism 20A, four color separation prism 20A can restrain a light quantity of the IR component received by IR image sensor 230 from decreasing due to prism transmission. Four color separation prism 20A can acquire a clearly captured image of the affected area, based on fluorescence generated by the light of the IR component being emitted to a fluorescent substance (for example, ICG) inside the affected area.

In FIG. 5, blue color separation prism 221 is disposed closer to the object side, subsequently (secondly) to IR separation prism 220. The reason is that the B-component has a shorter wavelength than that of the R-component and the G-component. As the wavelength becomes shorter, each color separation prism receives less influence of polarized light which can occur when the light is reflected. Therefore, since in four color separation prism 20A, blue color separation prism 221 is disposed closer to the object side than red color separation prism 222 and green color separation prism 223, it is possible to restrain the influence of the polarized light.

Blue color separation prism 221 is disposed closer to the object side than IR separation prism 220. In this case, in view of the spectroscopic properties of blue light reflective film 241 used for blue color separation prism 221, spectral transmittance becomes higher on a high wavelength side (that is, the green color component side and the red color component side) in FIG. 8. Accordingly, a reflected amount of the IR light increases in blue light reflective film 241, thereby decreasing the light quantity of the IR light incident on IR separation prism 220 disposed in the rear stage.

Therefore, in endoscope 10, since IR separation prism 220 is disposed closer to the object side than blue color separation prism 221 as illustrated in FIG. 5, an image obtained by the IR light can have higher image quality compared to a case where blue color separation prism 221 is disposed closer to the object side than IR separation prism 220. That is, based on the fluorescence of the ICG, endoscope 10 can acquire an image which clearly shows a state of the affected area.

Green color separation prism 223 and green color image sensor 233 are disposed so as to receive the light by setting incident light center line ILC as substantially the center. In this manner, without a need to dispose a green light reflective film, it is possible to simplify a shape of green color separation prism 223. Accordingly, it is possible to easily design a configuration element relating to the G-component.

It is preferable that the order of green color separation prism 223 is the last to receive the incident light. That is, is preferable that green color separation prism 223 is disposed farthest from the object side among a plurality of color separation prisms. The G-component is included in an intermediate wavelength band between the B-component and the R-component. In a front stage from green color separation prism 223, IR reflective film 240, blue light reflective film 241, and red light reflective film 242 can easily block light components other than the G-component. These reflective films can be designed as a low pass filter (LPF) or a high pass filter (HPF). Accordingly, it is possible to easily design filters.

Second Structure Example of Four Color Separation Prism

Figure 6:
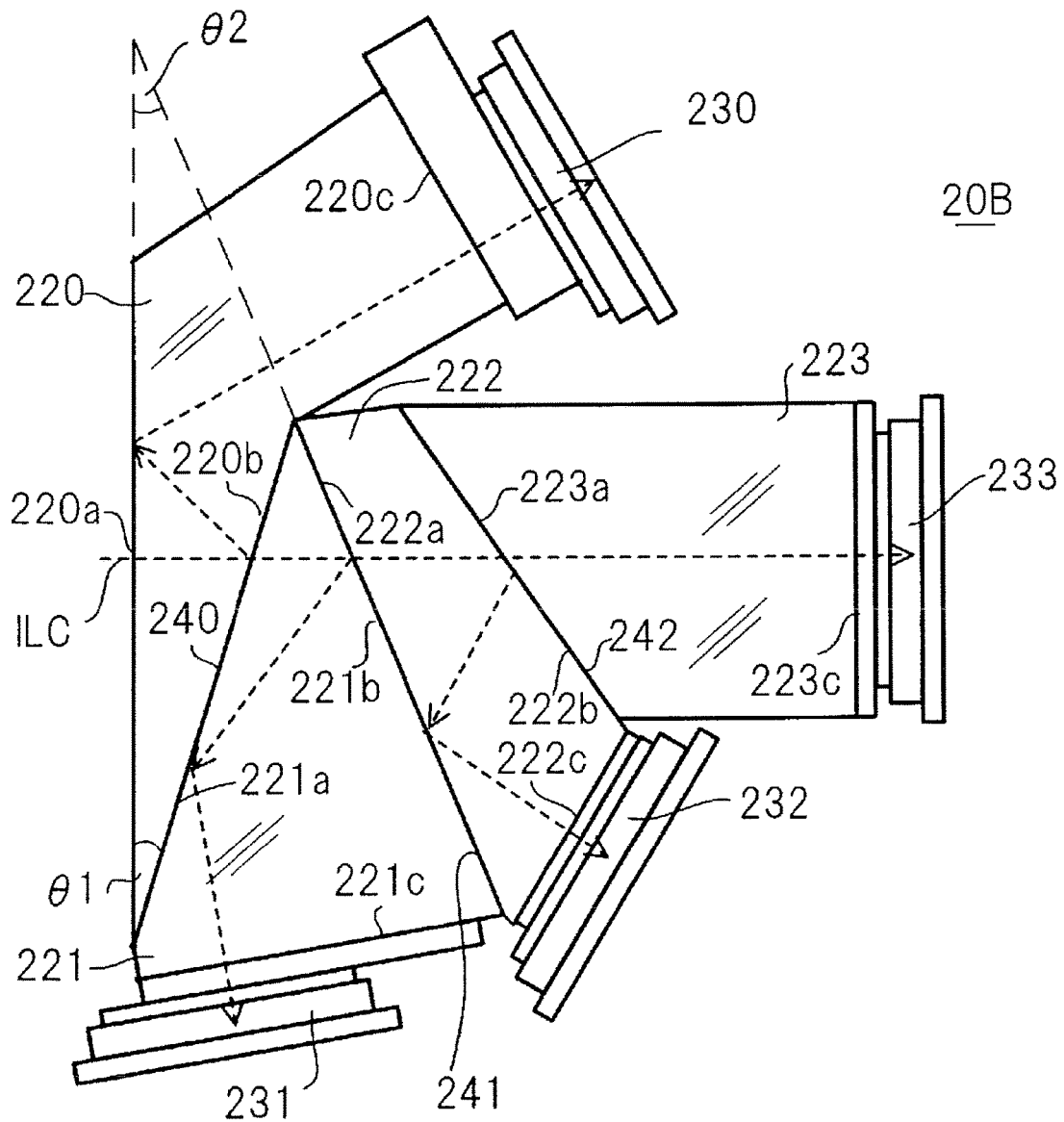
FIG. 6 a view illustrating a second structure example of the four color separation prism.

FIG. 6 a view illustrating a second structure example (four color separation prism 20B) of four color separation prism 20. In four color separation prism 20B, description of the same structure as that of four color separation prism 20A illustrated in FIG. 5 will be omitted or simplified.

Compared to four color separation prism 20A described above, four color separation prism 20B satisfies $\theta 2 > \theta 1$. Since angles are different from each other in this way, each color separation prism has a mutually different shape, orientation, and size. Through detailed consideration of the present inventor, it is found that a case of $\theta 2 = \theta 1$ also adopts the same configuration as that of four color separation prism B illustrated in FIG. 6.

IR image sensor 230 causes the light reflected on reflective surface 220b and object side incident surface 220a to be incident thereon, thereby receiving the light. Angle $\theta 1$ illustrated in FIG. 6 is smaller than angle $\theta 1$ illustrated in FIG. 5. Accordingly, a reflective angle (angle formed between a line perpendicular to reflective surface 220b and a light ray reflected from reflective surface 220b) on reflective surface 220b of IR separation prism 220 becomes smaller than that in a case illustrated in FIG. 5. Similarly, a reflective angle (angle formed between a line perpendicular to object side incident surface 220a and a light ray reflected from object side incident surface 220a) on object side incident surface 220a also becomes smaller than that in the case illustrated in FIG. 5.

Therefore, an orientation of the light ray reflected on object side incident surface 220a is close to an orientation of the light ray moving forward in green color separation prism 223, and a position of IR image sensor 230 is close to a position of green color image sensor 233.

In order to secure a required optical path length, IR separation prism 220 is designed so that a distance between object side incident surface 220a and light emission surface 220c is longer than that in a case illustrated in FIG. 5. Accordingly, reflective surface 220b of IR separation prism 220 is bent along the light ray reflected on object side incident surface 220a, and thus, a shape of IR separation prism 220 is complicated. Reflective surface 220b requires polishing in order to transmit the light components other than the IR component. However, if reflective surface 220b is bent, reflective surface 220b is less likely to be polished.

In this way, a front end portion of IR separation prism 220 (end portion including light emission surface 220c and IR image sensor 230) is formed close to green color separation prism 223 side. Accordingly, compared to the case illustrated in FIG. 5, it becomes more difficult to dispose red color separation prism 222 between the front end portion of IR separation prism 220 and green color separation prism 223. Therefore, red color separation prism 222 together with blue color separation prism 221 is disposed on the lower side from incident light center line ILC.

Blue color image sensor 231 causes the light reflected on reflective surface 221b and object side incident surface 221a to be incident thereon, thereby receiving the light. Angle θ2 illustrated in FIG. 6 is larger than angle θ2 illustrated in FIG. 5. Accordingly, a reflective angle (angle formed between a line perpendicular to reflective surface 221b and a light ray reflected from reflective surface 221b) on reflective surface 221b of blue color separation prism 221 becomes larger than that in the case illustrated in FIG. 5. Similarly, a reflective angle (angle formed between a line perpendicular to object side incident surface 221a and a light ray reflected from object side incident surface 221a) on object side incident surface 221a also becomes larger than that in the case illustrated in FIG. 5.

Therefore, the light reflected on object side incident surface 221a and emitted from light emission surface 221c is close to the incident surface of four color separation prism 20B (that is, object side incident surface 220a of IR separation prism 220), and is received in an end portion on object side incident surface 220a in blue color image sensor 231.

Design is made so as to satisfy the following condition. The light reflected on reflective surface 221b of blue color separation prism 221 does not go beyond a range of object side incident surface 221a, and is reflected on object side incident surface 221a. The light is totally reflected on object side incident surface 221a.

Next, pixel addition will be described.

IR image sensor 230 may output an electric signal having each pixel value (signal level) without any change. However, IR image sensor 230 may output the electric signal having a pixel value subjected to H/V pixel addition processing by performing the H/V pixel addition processing for adding pixel values of pixels adjacent in a horizontal (H) or vertical (V) direction.

If H/V pixels are added, for example, in a case where the pixel value of IR image sensor 230 is approximately "30", the pixel value of the IR component becomes "120" (=30×4) by adding the pixels.

If it is assumed that the pixel value of the IR component in the related art is approximately "10", IR image sensor 230 is independently disposed according to endoscope 10 of the present exemplary embodiment. Accordingly, compared to a case in the related art, the pixel value of the IR component can be obtained as much as approximately 3 times to 12 times.

It is assumed that the pixel value of respective RGB image sensors 231, 232, and 233 according to the present exemplary embodiment is approximately "100". In this case, if the H/V pixel addition processing is added, each signal level of the R-component, the G-component, and the B-component becomes substantially the same as a signal level of the IR component. Accordingly, the RGB image and the IR image are likely to be visible. The RGB image is obtained using at least one signal of the R-component, the G-component, and the B-component. The IR image is obtained using the signal of the IR component.

Sensor Sensitivity of Image Sensor

Figure 7:
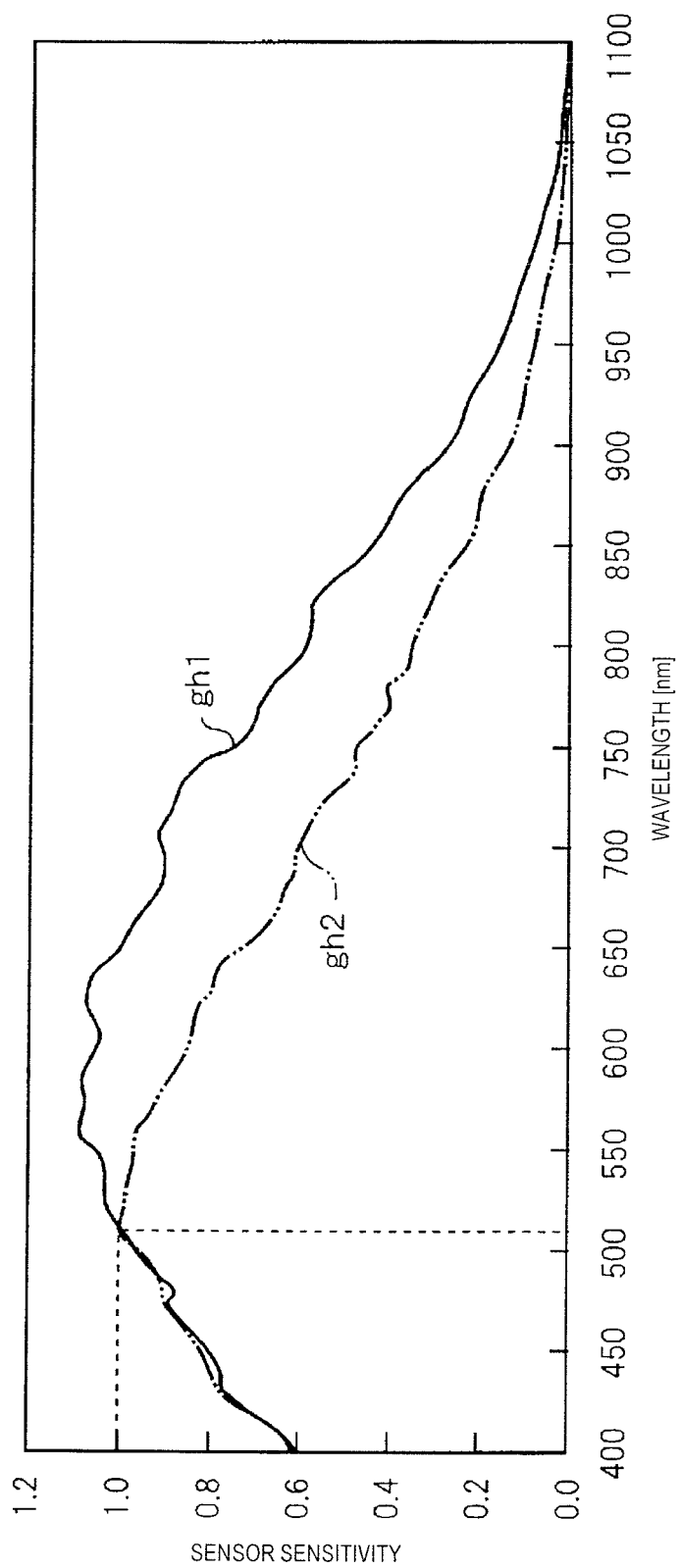
FIG. 7 is a graph illustrating an example of sensor sensitivity of the image sensor.

FIG. 7 is a graph illustrating sensor sensitivity of image sensor 230. The vertical axis represents the sensor sensitivity. The sensor sensitivity corresponds to a ratio of the light quantity detected by image sensor 230 with respect to the light quantity of the light incident on image sensor 230. The sensor sensitivity illustrated in FIG. 7 is an absolute value in a case where the sensor sensitivity in the light wavelength of 510 nm is set to value 1. The horizontal axis represents the light wavelength in units of nm. Waveform gh1 represents properties of the sensor sensitivity of image sensor 230 according to the present exemplary embodiment with respect to the light wavelength. Waveform gh2 represents properties of the sensor sensitivity of an image sensor according to a comparative example (in the related art) with respect to the light wavelength.

In a case of image sensor 230 according to the present exemplary embodiment, as illustrated by waveform gh1, the sensor sensitivity in the light wavelength of 830 nm is value 0.551, which is approximately 55% compared to a case of the light wavelength of 510 nm. On the other hand, in a case of the image sensor according to the comparative example, as illustrated by waveform gh2, the sensor sensitivity in the light wavelength of 830 nm is value 0.298, which is approximately 30% compared to the case of the light wavelength of 510 nm. The wavelength band of 830 nm is the wavelength band of the fluorescence using the ICG.

Compared to the sensor sensitivity of the image sensor according to the comparative example, the sensor sensitivity of image sensor 230 according to the present exemplary embodiment is substantially the same sensitivity in a blue light region (B-component) of 400 nm to 500 nm. However, the sensor sensitivity of image sensor 230 becomes higher in a green light region (G-component) of 500 nm to 600 nm and a red light region (R-component) of 600 nm to 700 nm. Furthermore, compared to the sensor sensitivity of the image sensor according to the comparative example, the sensor sensitivity of image sensor 230 is high even in a near infrared light (IR light) region (IR component) of 750 nm to 900 nm.

Hereinafter, an image sensor having the properties of the sensor sensitivity illustrated by waveform gh1 is referred to as a high sensitivity sensor. An image sensor having the properties of the sensor sensitivity illustrated by waveform gh2 is referred to as a normal sensitivity sensor. As can be understood from FIG. 7, the high sensitivity sensor has high sensitivity on the long wavelength side, compared to the normal sensitivity sensor.

In the first exemplary embodiment, the high sensitivity sensor is used for image sensors 230 to 233. Although the high sensitivity sensor is used for red color, green color, and blue color image sensors 231 to 233, the normal sensitivity sensor may be used.

Spectroscopic Properties of Four Color Separation Prism

Figure 8:
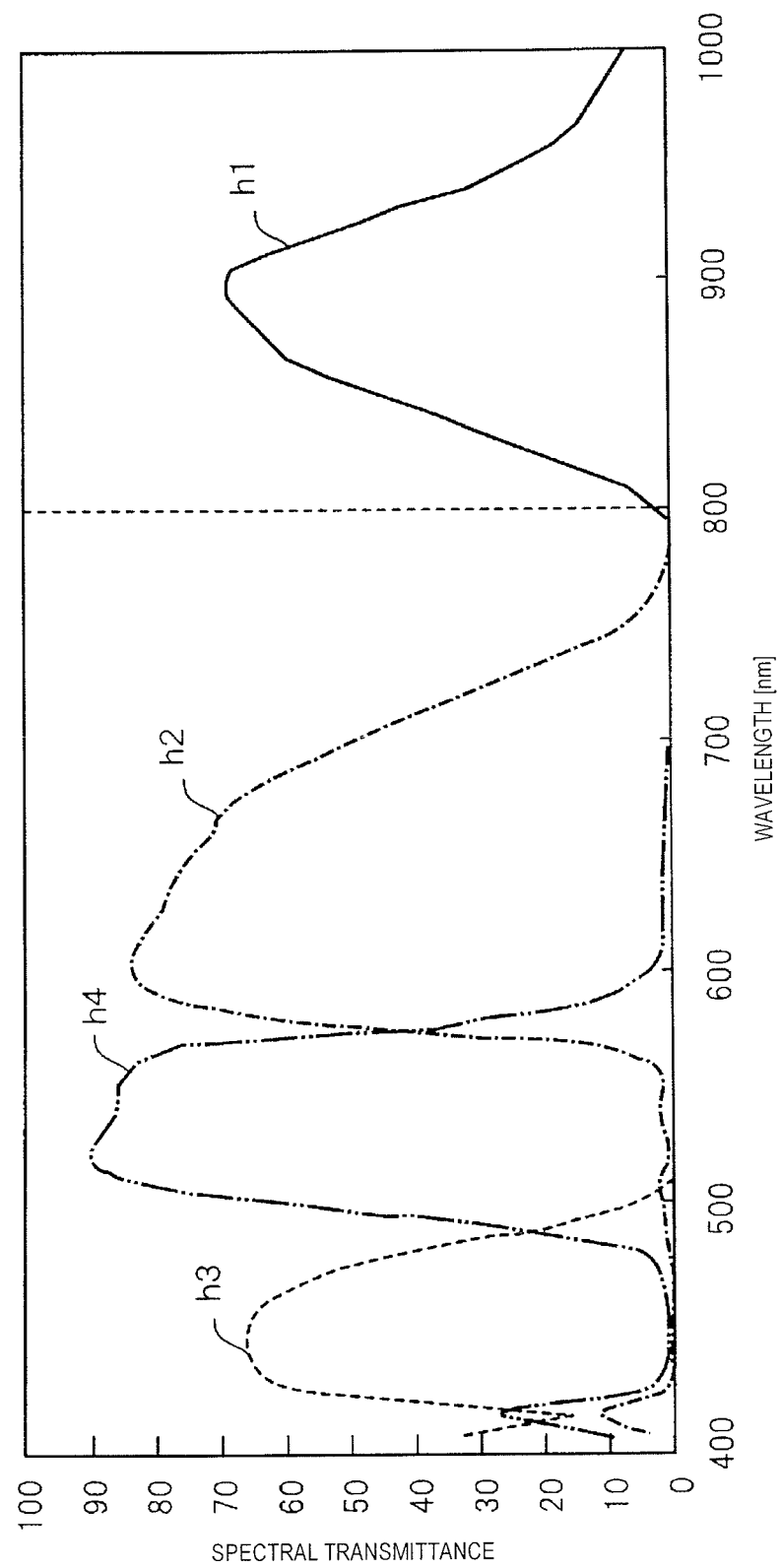
FIG. 8 is a graph illustrating an example of spectroscopic properties of the four color separation prism.

FIG. 8 is a graph illustrating an example of spectroscopic properties (spectral transmittance) of four color separation prism 20. The vertical axis in FIG. 8 represents each spectral transmittance (%), and corresponds to a ratio of the light quantity of the light incident on image sensors 230 to 233 in each prism with respect to the light quantity of the light incident on each prism. The horizontal axis in FIG. 8 represents the wavelength (nm) of the light incident on respective image sensors 230 to 233. The light quantity of the light incident on image sensors 230 to 233 in each prism corresponds to the light quantity of the light emitted from each prism.

In FIG. 8, waveform h1 (solid line) illustrates the spectroscopic properties of the light of the IR component which is incident on IR image sensor 230. Transmittance of the light of the IR component which is incident on IR image sensor 230 in the light incident on four color separation prism 20 has a peak waveform whose wavelength is near 900 nm in the wavelength of 800 to 1,000 nm and whose transmittance is approximately 70%.

Waveform h2 (one-dot chain line) illustrates the spectroscopic properties of the light of the R-component which is incident on red color image sensor 232. Transmittance of the light of the R-component which is incident on red color image sensor 232 has a peak waveform whose wavelength is near 600 nm and whose transmittance is approximately 80%.

Waveform h3 (dotted line) illustrates the spectroscopic properties of the light of the B-component which is incident on blue color image sensor 231. Transmittance of the light of the B-component which is incident on blue color image sensor 231 has a peak waveform whose wavelength is near 450 nm and whose transmittance exceeds 60%.

Waveform h4 (two-dot chain line) illustrates the spectroscopic properties of the light of the G-component which is incident on green color image sensor 233. Transmittance of the light of the G-component which is incident on green color image sensor 233 has a peak waveform whose wavelength is near 530 nm and whose transmittance is approximately 90%.

In this way, any transmittance of the light of the IR component, the R-component, the B-component, and the G-component which are separated by four color separation prism 20 exceeds 60%. Therefore, each pixel value of the IR component, the R-component, the B-component, and the G-component can be suitably obtained, and a signal of the IR component may not be greatly amplified. In this manner, in a case where the affected area is imaged, color reproducibility of a captured image including the IR component is improved.

Spectral Sensitivity of Quadruple Board-Type Camera

Figure 9:
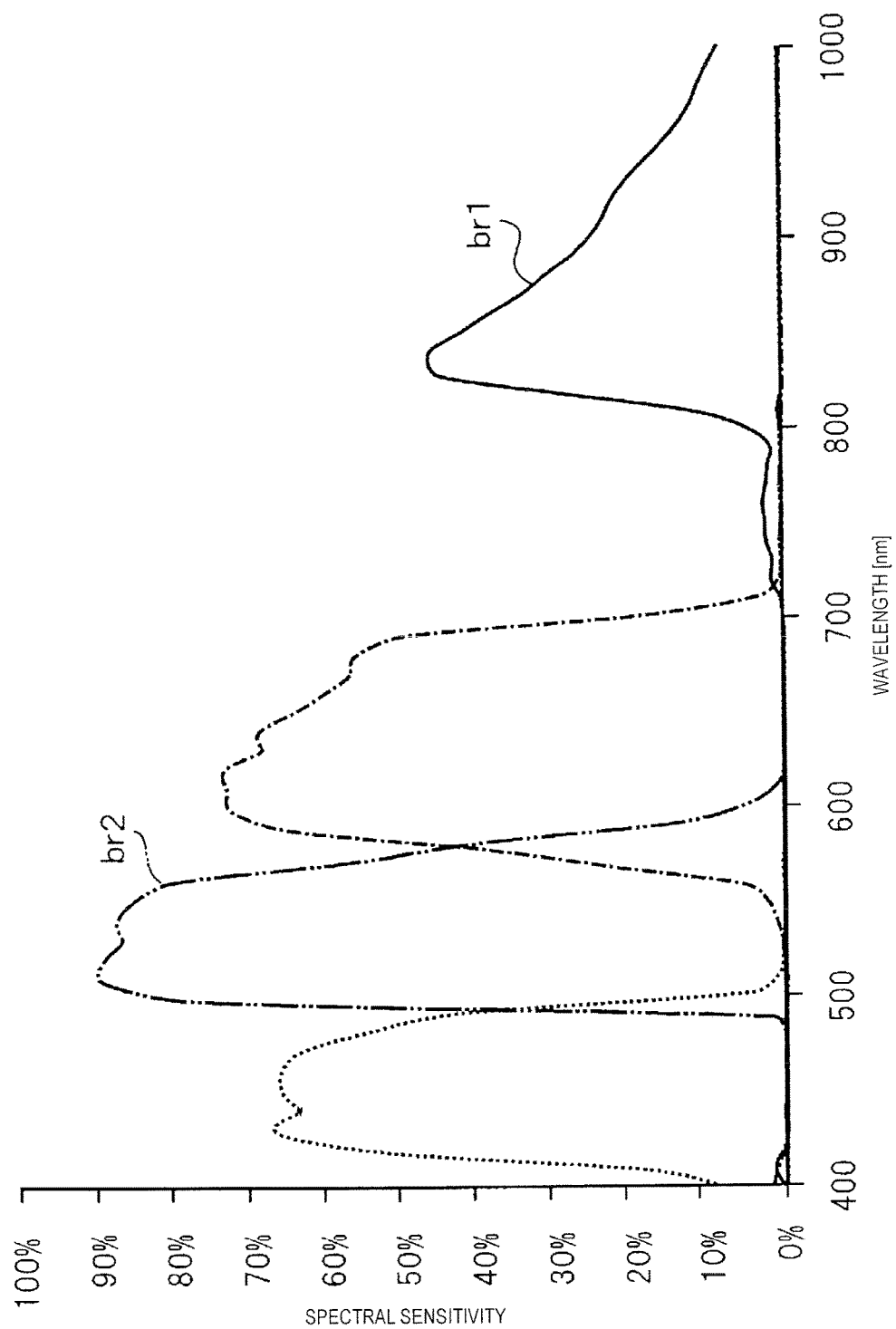
FIG. 9 is a graph illustrating spectral sensitivity in a case where four image sensors are used.

FIG. 9 is a graph illustrating the spectral sensitivity in a case where four image sensors 230 to 233 are used. The vertical axis in FIG. 9 represents the spectral sensitivity in units of percentage. The horizontal axis in FIG. 9 represents a wavelength (nm) of the light incident on respective image sensors 230 to 233. The spectral sensitivity corresponds to the light quantity of the light having each wavelength detected by image sensors 230 to 233 with respect to the light quantity of the light incident on four color separation prism 20. The spectral sensitivity is obtained in such a way that the sensor sensitivity illustrated in FIG. 7 is multiplied by the spectral transmittance illustrated in FIG. 8. The spectral sensitivity is one of performance indicators of the quadruple board-type camera inside camera head 14. In FIG. 9, the maximum value of the sensor sensitivity of the normal sensitivity sensor illustrated by waveform gh6 in FIG. 7 (sensor sensitivity in a case where the wavelength is 510 nm in both the normal sensitivity sensor and the high sensitivity sensor) is set to value 1. In this manner, value 1 is multiplied by the spectral transmittance of four color separation prism 20. Therefore, the spectral sensitivity of 100% indicates a state where the spectral transmittance of four color separation prism 20 is 100% and the sensor sensitivity of the normal sensitivity sensor is the maximum.

The spectral sensitivity illustrated in FIG. 9 has each high value in a blue light region, a green light region, a red light region, and a near infrared light region, when the light passes through four color separation prism 20.

Here, a peak value of the spectral sensitivity in the green light region (wavelength band including 530 nm) is approximately 90% (refer to waveform br2). On the other hand, a peak value of the spectral sensitivity in the near infrared light region (wavelength band including 830 nm) is approximately 48%, and has a value equal to or greater than 40% of the peak value (90%) of the spectral sensitivity in the green light region (530 nm) (refer to waveform br1). Therefore, the spectral sensitivity in the IR region is obtained so as to have a desired high value. Here, the peak value of the spectral sensitivity in the green light region corresponds to the maximum value of the spectral sensitivity in all of the wavelength bands including the visible light band of the RGB. Although not illustrated, in the related art, the peak value of the spectral sensitivity in the near infrared light region is approximately half (approximately 24%) of the spectral sensitivity of the quadruple board-type camera according to the present exemplary embodiment.

In this way, the quadruple board-type camera included in camera head 14 has a peak value of 40% equal to or greater than a peak value in the visible light region (here, a peak value in the green light region). That is, the quadruple board-type camera has high sensitivity for the IR light.

The sensor sensitivity of the image sensors illustrated in FIGS. 7 to 9, the spectroscopic properties of four color separation prism 20, and the spectral sensitivity of the quadruple board-type camera are examples, the endoscope system may have other properties.

Configuration of Endoscope System

FIG. 10 is a block diagram illustrating a configuration of endoscope system 5 according to the first exemplary embodiment. Endoscope system 5 is configured to include endoscope 10, CCU 30, and display 40. CCU 30 is an example of a processor. Display 40 is an example of a display device. Camera head 14 of endoscope 10 has four color separation prism 20, and image sensors 230, 231, 232, and 233 which are described above. In FIG. 10, camera head 14 further has respective element drivers 141$i$, 141$r$, 141$b$, and 141$g$, drive signal generator 142, synchronizing signal generator 143, and signal output 145.

Element driver 141$i$ drives image sensor 230 in accordance with a drive signal. Element driver 141$r$ drives image sensor 231 in accordance with a drive signal. Element driver 141$b$ drives image sensor 232 in accordance with a drive signal. Element driver 141$g$ drives image sensor 233 in accordance with a drive signal.

Drive signal generator 142 generates the drive signal for respective element drivers 141$i$, 141$r$, 141$b$, and 141$g$. Synchronizing signal generator 143 corresponds to a function of a timing generator (TG) circuit, and supplies a synchronizing signal (timing signal) to drive signal generator 142.

Signal output 145 transmits an electric signal output from image sensors 230, 231, 232, and 233 to CCU 30 via signal cable 14$z$ by using an LVDS method, for example. Signal output 145 may transmit a synchronizing signal output from synchronizing signal generator 143 to CCU 30 via signal cable 14$z$. Signal output 145 may transmit an operation signal of operation switch 19 to CCU 30 via signal cable 14$z$. Signal output 145 corresponds to a function of a signal output circuit.

CCU 30 fulfills various functions by executing a program stored in an internal or external memory (not illustrated) of CCU 30. The various functions include each function of RGB signal processor 22, IR signal processor 23, and output 28.

RGB signal processor 22 converts the electric signals of the B-component, the R-component, and the G-component which are output from image sensors 231, 232, and 233, into video signals which can be displayed on display 40, and outputs the video signals to output 28.

IR signal processor 23 converts the electric signal of the IR component output from image sensor 230 into a video signal, and outputs the video signal to output 28. IR signal processor 23 may have gain adjuster 23z. Gain adjuster 23z adjusts an amplification degree (gain) when the electric signal of the IR component which is output from IR image sensor 230 is converted into the video signal. For example, gain adjuster 23z may adjust signal strength of the video signal of the RGB component so as to be substantially the same as signal strength of the video signal of the IR component.

Gain adjuster 23z enables a user to reproduce the IR image for the RGB image with optional intensity. Instead of adjusting the amplification degree of the electric signal of the IR component, or in conjunction with the adjustment, RGB signal processor 22 may adjust the amplification degree of the electric signal of the RGB component.

When signal processing is performed, RGB signal processor 22 and IR signal processor 23 receives the synchronizing signal output from synchronizing signal generator 143, and are operated in accordance with the synchronizing signal. In this manner, an image (video image) of each RGB color component and an image of the IR component are adjusted so as not to cause a time lag.

In accordance with the synchronizing signal output from synchronizing signal generator 143, output 28 outputs at least any one of the video signal of each RGB color component and the video signal of the IR component, to display 40. For example, output 28 outputs the video signal, based on any one of a dual output mode and a superposed output mode.

During the dual output mode, output 28 simultaneously outputs RGB image G1 and IR image G2 (refer to FIG. 11) using different screens. The dual output mode enables a user to observe the affected area tg by comparing the RGB image and the IR image with each other using the different screens.

Figure 12:
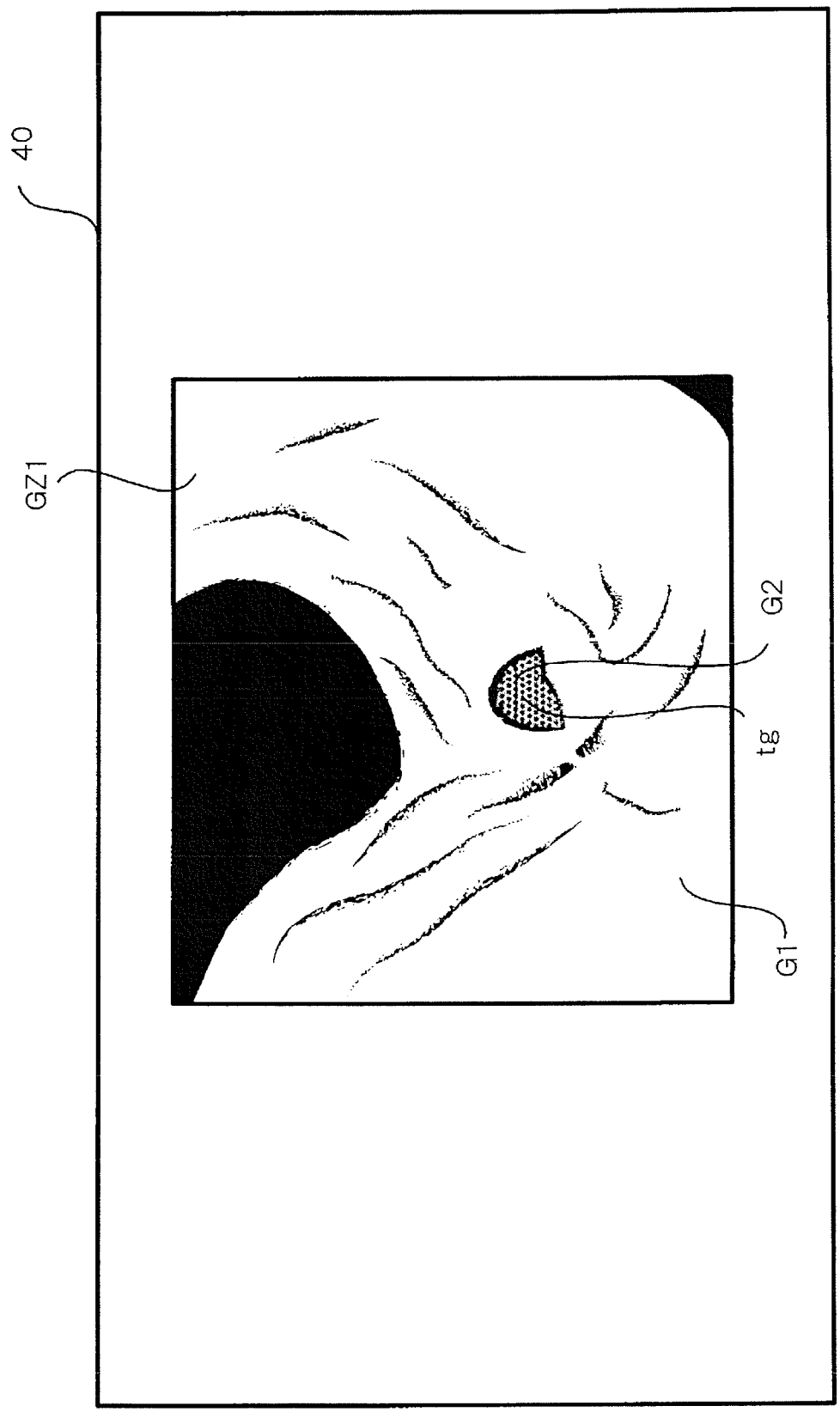
FIG. 12 a schematic view illustrating an image during a superposed output mode displayed on the display.

During the superposed output mode, output 28 outputs synthesized image GZ in which the RGB image and the IR image are superposed on each other (refer to FIG. 12). For example, the superposed output mode enables a user to clearly observe affected area tg which fluoresces due to the ICG and the IR light serving as illumination light inside the RGB image.

An example has been described in which RGB signal processor 22, IR signal processor 23, and output 28 perform processing using software by the processor inside CCU 30 cooperating with the memory. However, all of these may be configured to respectively include dedicated hardware.

Based on the video signal output from CCU 30, display 40 causes a screen to display an image of an object such as affected area tg which is imaged by endoscope 10 and which is output from CCU 30. In a case of the dual output mode, display 40 divides the screen into a plurality of screens (for example, into two screens), and causes each screen to display RGB image G1 and IR image G2 side by side (refer to FIG. 11). In a case of the superposed output mode, display 40 causes one screen to display synthesized image GZ in which RGB image G1 and IR image G2 are superposed on each other (refer to FIG. 12).

In this way, in endoscope system 5, in a case where an area inside a body is imaged using endoscope 10, an indocyamine green (ICG) which is a fluorescent substance may be administered into the body, and near infrared light may be emitted to an area such as an excessively accumulated tumor (affected area). The affected area may be lightened so as to image the affected area.

Light L which is introduced into light source connector 18 by a user operating operation switch 19 is guided to a front end side of scope 11, and is emitted from imaging window 11z, thereby illuminating an area around the affected area which includes the affected area. The light reflected on the affected area and the like is guided to a rear end side of scope 11 through imaging window 11z, is focused by relay lens 13, and is incident on four color separation prism 20 of camera head 14.

In four color separation prism 20, the light of the IR component separated by IR separation prism 220 in the incident light forms an image as an optical image of the infrared light component in IR image sensor 230. The light of the B-component separated by blue color separation prism 221 forms an image as an optical image of the blue color component in blue color image sensor 231. The light of the R-component separated by red color separation prism 222 forms an image as an optical image of the red color component in red color image sensor 232. The light of the G-component separated by green color separation prism 223 forms an image as an optical image of the green color component in green color image sensor 233.

The electric signal of the IR component which is converted by IR image sensor 230 is converted into the video signal by IR signal processor 23 inside CCU 30, and is output to output 28. Each electric signal of the B-component, the R-component, and the G-component which are respectively converted by visible light image sensors 231, 232, and 233 are converted into each video signal by RGB signal processor 22 inside CCU 30, and is output to output 28. The video signal of the IR component and the respective video signals of the B-component, the R-component, and the G-component are synchronized with each other, and are output to display 40.

Figure 11:
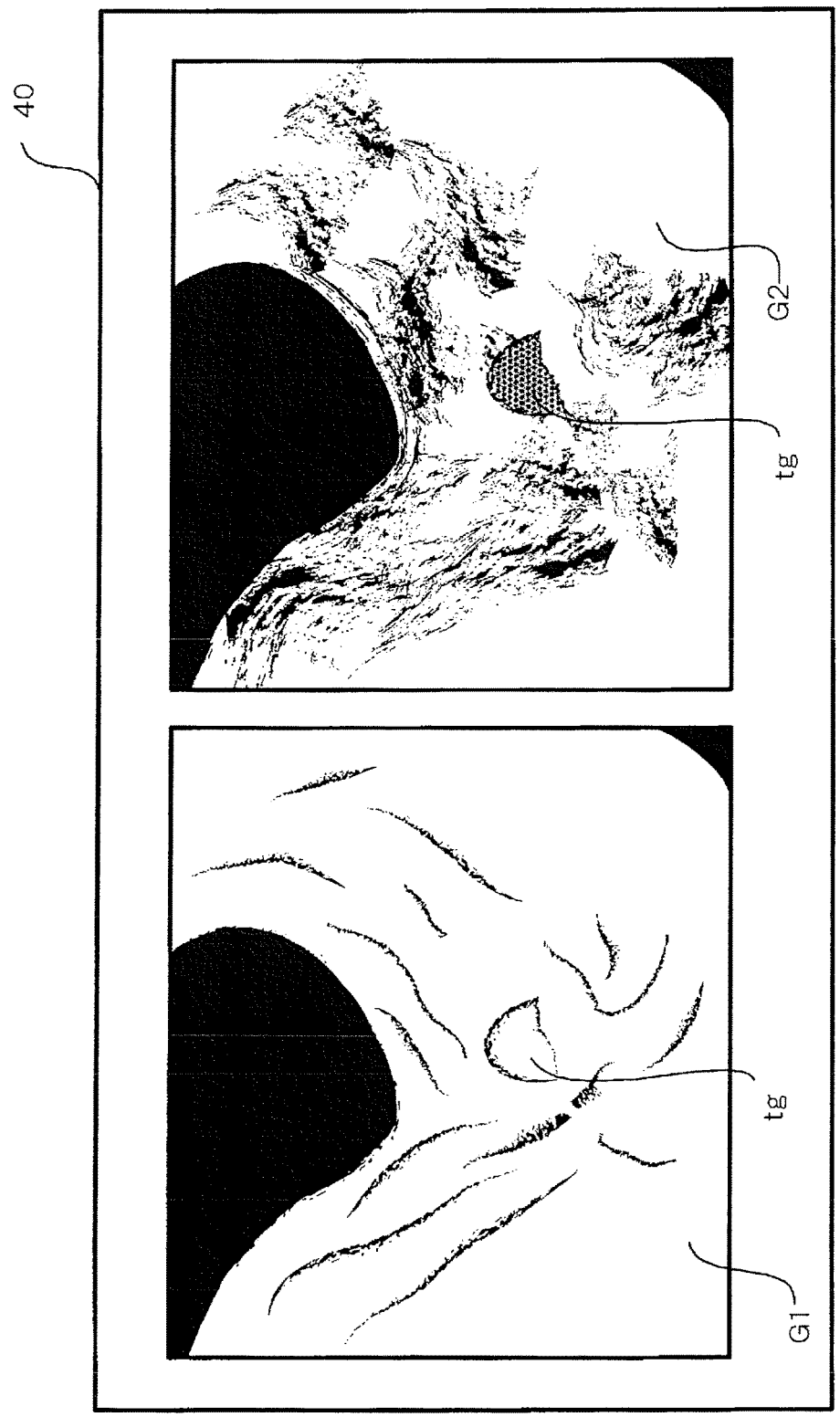
FIG. 11 is a schematic view illustrating an image during a dual output mode displayed on a display.

In a case where output 28 sets the dual output mode, display 40 causes two screen to simultaneously display RGB image G1 and IR image G2. FIG. 11 is a schematic view illustrating an image during the dual output mode displayed on display 40. RGB image G1 is a color image by imaging the area including affected area tg after emitting the visible light thereto. IR image G2 is a black and white image (any optional color can be set) by imaging the area including affected area tg after emitting the IR light thereto.

In a case where output 28 sets the superposed output mode, display 40 displays synthesized image GZ1 in which RGB image G1 and IR image G2 are superposed on (synthesized with) each other. FIG. 12 a schematic view illustrating an image during the superposed output mode displayed on display 40.

Advantageous Effect

In this way, endoscope 10 according to the present exemplary embodiment includes four color separation prism 20 that includes the first color separation prism, the second color separation prism, the third color separation prism, and the fourth color separation prism which respectively separate the light reflected from the affected area into the first color component, the second color component, the third color component, and the fourth color component which are any one of the blue color component, the red color component, the green color component, and the IR component, the first color image sensor that is installed in the first color separation prism, and that converts the separated first color component into the electric signal, the second color image sensor that is installed in the second color separation prism, and that converts the separated second color component into the electric signal, the third color image sensor that is installed in the third color separation prism, and that converts the separated third color component into the electric signal, the fourth color image sensor that is installed in the fourth color separation prism, and that converts the separated fourth color component into the electric signal, and signal output 145 that outputs the color image signal and the IR signal from the respective converted electric signals. The first color separation prism, the second color separation prism, the third color separation prism, and the fourth color separation prism are sequentially disposed from the object side when receiving the light incident from the affected area. The first color image sensor is disposed opposite to the second color image sensor and the third color image sensor across the incident ray which is incident vertically to the object side incident surface of the first color separation prism. For example, the incident ray is incident light center line ILC.

In this manner, endoscope 10 can usefully and efficiently dispose each color separation prism (particularly, the third color separation prism), and can easily realize four color separation prism 20. For example, due to the layout position of the first color separation prism and the first color image sensor, the layout space for the third color separation prism is small on the upper side of the incident ray (one region with respect to the incident ray). However, the layout space can be secured on the lower side of the center line of the incident ray (the other region with respect to the incident ray). Accordingly, four color separation prism 20 can be mounted on endoscope 10, and each independent image sensor can receive each color component separated by each color separation prism. Therefore, the light strength of each color component is likely to be secured. Accordingly, although the light emitting amount is small in the fluorescence, endoscope 10 improves image quality by adding the infrared light component to the image. Endoscope 10 can adjust color balance by independently controlling each color component, and can improve color reproducibility of each color component.

Second Exemplary Embodiment

In the first exemplary embodiment, the quadruple board-type prism has been described. In a second exemplary embodiment, a triple board-type prism will be described which separates the light into the IR light and three of the B-light, R-light, and G-light. That is, camera head 14 includes a three color separation prism and three image sensors. The IR light is separated using the blue color separation prism, and is received by the image sensor.

In the present exemplary embodiment, the same reference numerals will be given to the same matters as those in the first exemplary embodiment, and description thereof will be omitted or simplified.

Figure 14:
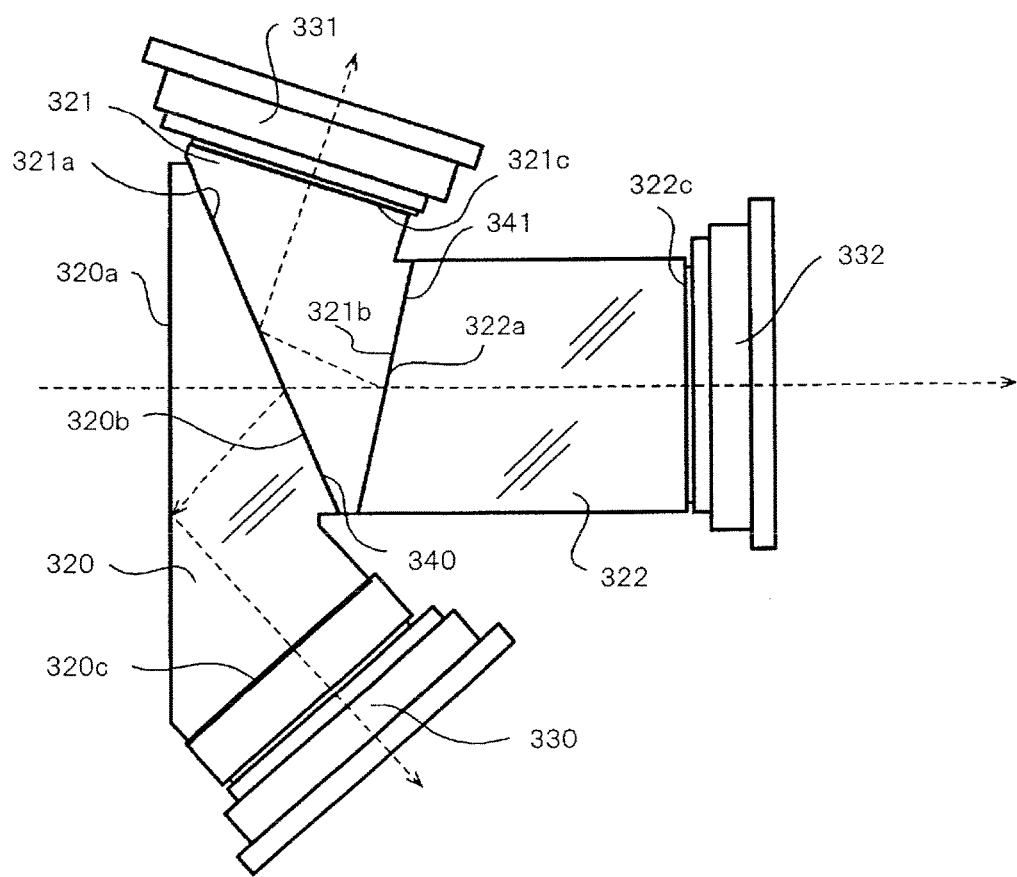
FIG. 14 is a view illustrating a structure example of a three color separation prism according to a second exemplary embodiment.

FIG. 14 is a view illustrating a structure example of three color separation prism 20A according to the second exemplary embodiment. Three color separation prism 20A separates the incident light guided by relay lens 13 into the R-light, G-light, B-light, and IR light. In three color separation prism 20A, IR and blue color separation prism 320, red color separation prism 321, and green color separation prism 322 are sequentially assembled in the optical axis direction.

IR and blue color image sensor 330 is disposed to face light emission surface 320c of IR and blue color separation prism 320. Red color image sensor 331 is disposed to face light emission surface 321c of red color separation prism 321. Green color image sensor 332 is disposed to face light emission surface 322c of green color separation prism 322.

For example, image sensors 330 to 332 are CCD or CMOS image sensors including respective pixels which are arrayed in a horizontal (H) direction and a vertical (V) direction. Image sensors 330 to 332 convert the optical image in which the light separated into each color of IR, B, R, and G forms an image on each imaging surface, into the electric signal. The IR light is detected by IR and blue color image sensor 330, and thus, the IR light glows in a blue color.

In IR and the blue color separation prism 320, the incident light is incident on incident surface 320a of IR and the blue color separation prism 320. The light reflected on reflective surface 320b facing incident surface 320a is totally reflected at a boundary of incident surface 320a of IR and blue color separation prism 320, and is incident on IR and blue color image sensor 330 after being emitted from light emission surface 320c facing incident surface 320a. For example, IR and blue light reflective film 340 is formed on reflective surface 320b by vapor deposition. IR and blue color separation prism 320 causes the light of the IR and blue color component in the incident light to be reflected thereon, and causes other light (light of the R-component and the G-component) to be transmitted therethrough. IR and blue color image sensor 330 causes the light reflected on reflective surface 320b and incident surface 320a to be incident thereon, thereby receiving the light. In this way, IR and blue color separation prism 320 is molded so that the light moves forward in IR and blue color separation prism 320.

In red color separation prism 321, the light (incident light) transmitted through IR and blue color separation prism 320 is incident on incident surface 321a of red color separation prism 321. The light reflected on reflective surface 321b facing incident surface 321a is totally reflected at a boundary of incident surface 321a of red color separation prism 321, and is incident on red color image sensor 331 after being emitted from light emission surface 321c facing incident surface 321a. For example, red light reflective film 341 is formed on reflective surface 321b by vapor deposition. Red color separation prism 321 causes the light of the R-component in the incident light to be reflected thereon, and causes other light (light of the G-component) to be transmitted therethrough. Red color image sensor 331 causes the light reflected on reflective surface 321b and incident surface 321a to be incident thereon, thereby receiving the light. In this way, red color separation prism 321 is molded so that the light moves forward in red color separation prism 321.

In green color separation prism 322, the light (incident light) transmitted through red color separation prism 321 is incident on incident surface 322a of green color separation prism 322, and is incident on green color image sensor 332 after being emitted from light emission surface 322c facing incident surface 322a. In this way, green color separation prism 322 is molded so that the light moves forward in green color separation prism 322.

In the triple board-type camera (three color separation prism 20A and image sensors 330 to 332), an optical distance (optical path length) from flange surface 13v of relay lens 13 to image sensors 330 to 332 is set to 17.526 mm in a case of the C-mount. A refractive index of three color separation prism 20A may be the same value as "1.8" which is a refractive index of four color separation prism 20. In a case of the triple board-type camera, there is more room in the layout space compared to the quadruple board-type camera. Accordingly, the refractive index of three color separation prism 20A may be a value of the refractive index which is slightly smaller than that of the quadruple board-type camera, for example, "1.7". Compared to the quadruple board-type camera, the refractive index is lowered to a slightly smaller value. In this manner, an actual distance (length) of the triple board-type camera is shortened.

Figure 15:
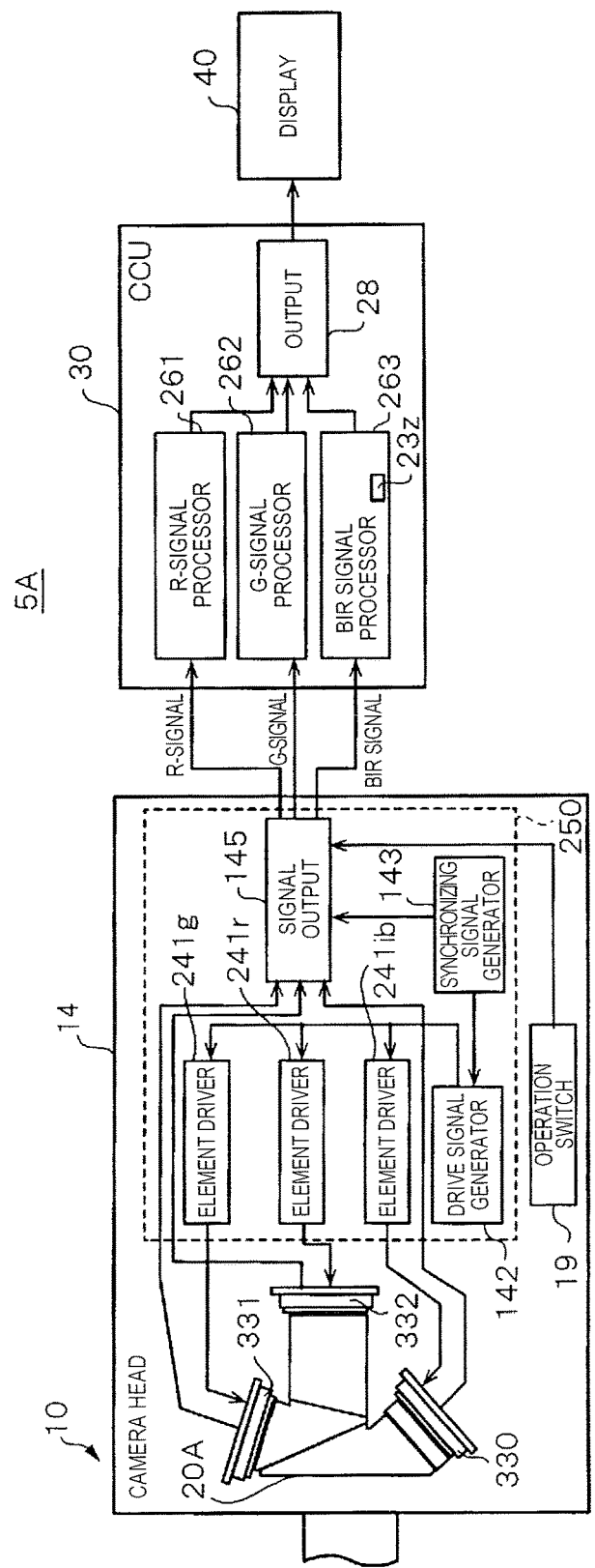
FIG. 15 is a block diagram illustrating a configuration example of an endoscope system according to the second exemplary embodiment.

FIG. 15 is a block diagram illustrating a configuration example of endoscope system 5A according to the second exemplary embodiment. The endoscope system according to the second exemplary embodiment has substantially the same configuration as that according to the first exemplary embodiment. The same reference numerals will be given to the same configuration elements as those according to the first exemplary embodiment, and description thereof will be omitted or simplified. Here, a configuration and an operation which are different from those according to the first exemplary embodiment will be mainly described.

According to the second exemplary embodiment, unlike the first exemplary embodiment, three element driver 241ib, element driver 241r, and element driver 241g are mounted on electronic board 250.

Element driver 241ib drives IR and blue color image sensor 330 in accordance with a drive signal. Element driver 241r drives red color image sensor 331 in accordance with a drive signal. Element driver 241g drives green color image sensor 332 in accordance with a drive signal.

Drive signal generator 142 generates the drive signals for each of element drivers 241ib, 241r, and 241g.

Signal output 145 transmits the electric signal output from image sensors 330, 331, and 332 to CCU 30A. According to the present exemplary embodiment, unlike the first exemplary embodiment, signal output 145 transmits the signal of the R-component (R-signal), the signal of the G-component (G-signal) and the signal (BIR signal) including at least one of the B-component and the IR component, to CCU 30A.

Instead of RGB signal processor 22 and IR signal processor 23, CCU 30A includes R-signal processor 261 for converting the R-signal into a video signal, G-signal processor 262 for converting the G-signal into a video signal, and BIR signal processor 263 for converting the BIR signal into a video signal. BIR signal processor 263 includes gain adjuster 23z. CCU 30A is the same as CCU 30 except for a configuration and an operation of the signal processor.

Figure 16:
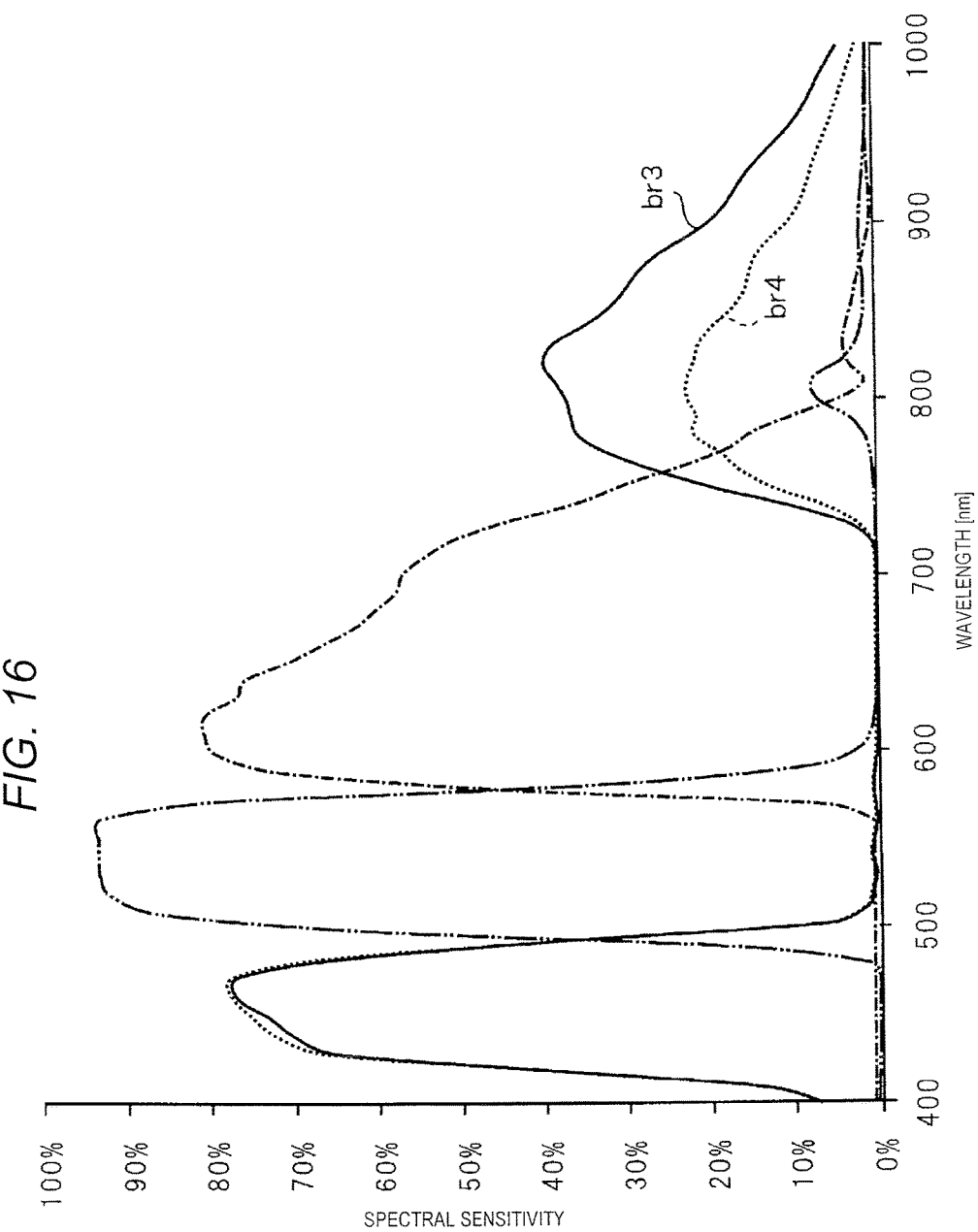
FIG. 16 is a graph illustrating spectral sensitivity in a case where three image sensors are used and one of the image sensors receives IR and blue light.

FIG. 16 is a graph illustrating spectral sensitivity in a case where three image sensors 330, 331, and 332 are used and one image sensor 330 receives the IR and blue color light. The vertical axis in FIG. 16 represents the spectral sensitivity in units of percentage. The horizontal axis in FIG. 16 represents a wavelength (nm) of the light incident on respective image sensors 330 to 332. The spectral sensitivity corresponds to the light quantity of the light having each wavelength detected by image sensors 330 to 332 with respect to the light quantity of the light incident on three color separation prism 20A. The spectral sensitivity is obtained in such a way that the sensor sensitivity illustrated in FIG. 6 is multiplied by the spectral transmittance of three color separation prism 20A. Although not illustrated, the spectral transmittance of three color separation prism 20A is the same as the spectral transmittance of four color separation prism 20 according to the first exemplary embodiment, for example. The spectral sensitivity is one of performance indicators of the triple board-type camera inside camera head 14.

IR and blue color image sensor 330 receives the light in the blue light region and the IR light through IR and the blue color separation prism 320. As IR and blue color image sensor 330, the high sensitivity sensor illustrated in the first exemplary embodiment is used. As red color image sensor 331 and green color image sensor 332, the high sensitivity sensor may be used, or the normal sensitivity sensor may be used.

FIG. 16 illustrates the spectral sensitivity (refer to waveform br3) in a case of using the high sensitivity sensor and the spectral sensitivity (refer to waveform br4) in a case of using the normal sensitivity sensor. Since endoscope 10 uses the high sensitivity sensor, the spectral sensitivity in the IR region can be improved.

In the graph illustrated in FIG. 16, a peak value of the spectral sensitivity near the wavelength of 580 nm in the green light region which is received by green color image sensor 332 is approximately 94%. On the other hand, a peak value of the spectral sensitivity near the wavelength of 830 nm in the IR region is approximately 40%. Therefore, the peak value of the spectral sensitivity in the IR region is approximately 42.5% (40%/94%) of the peak value of the spectral sensitivity in the visible light region (here, the wavelength of 580 nm), that is, 40% or greater. In this manner, the spectral sensitivity in the IR region can be obtained as a desired high value.

Here, as an comparative example, a case will be described where the green color image sensor receives the IR light.

Figure 17:
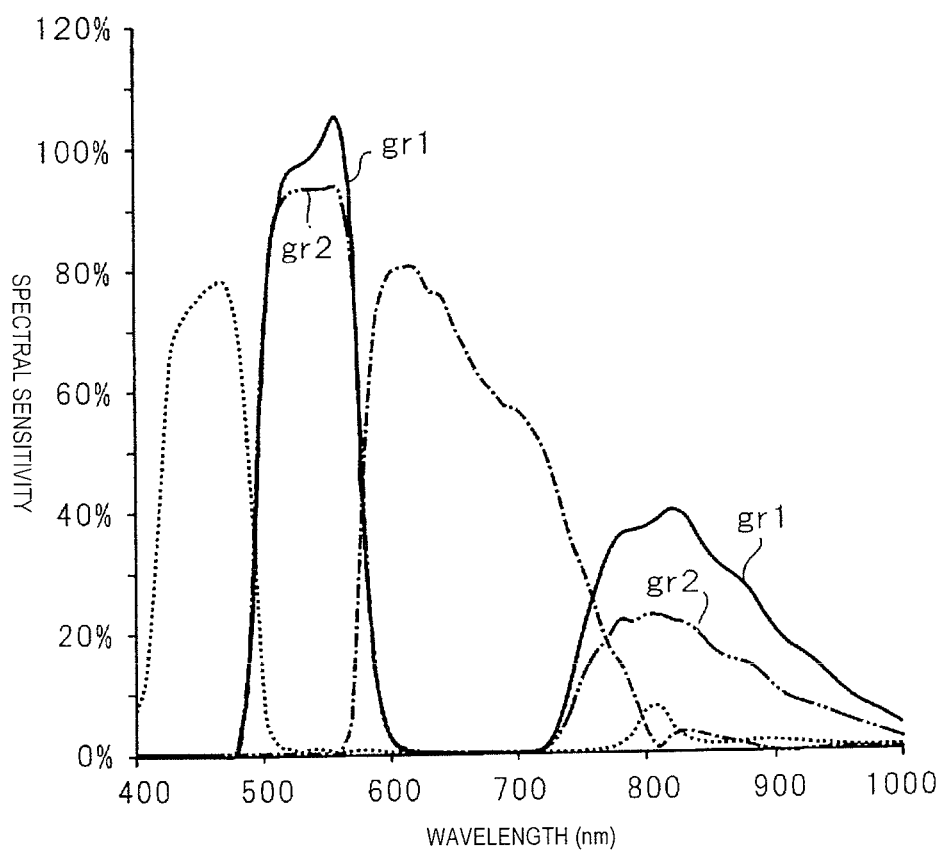
FIG. 17 is a graph illustrating spectral sensitivity in a case where an IR and green color image sensor according to the comparative example receives IR light.

FIG. 17 is a graph illustrating spectral sensitivity in a case where IR and green color image sensor 332x (not illustrated) receives the IR light, as the comparative example. IR and green color image sensor 332x receives the light in the green light region and the IR light through green color separation prism 322x. In the graph of the sensor sensitivity illustrated in FIG. 17, the sensor sensitivity of the high sensitivity sensor in the green light region (500 nm to 600 nm) becomes higher than that of the normal sensitivity sensor.

In the green light region, compared to the spectral sensitivity of the normal sensitivity sensor illustrated by waveform gr2 in FIG. 17, the spectral sensitivity of the high sensitivity sensor illustrated by waveform gr1 becomes higher. Therefore, in a case where IR and green color image sensor 332x is used, the light receiving sensitivity of the IR light can be improved. On the other hand, the color balance in the visible light region is disturbed, and the color reproducibility (distribution of the RGB color component) becomes poor.

In the graph illustrated in FIG. 17, the peak value of the spectral sensitivity of the wavelength of 580 nm in the green light region is approximately 105%. On the other hand, the peak value of the spectral sensitivity of the wavelength of 830 nm in the IR region is approximately 40%. That is, the peak value of the spectral sensitivity in the IR region is approximately 38% (40%405%) of the peak value of the spectral sensitivity in the green light region, that is, smaller than 40%. Therefore, as the spectral sensitivity in the IR region, it is difficult to obtain a desired value.

If the red color image sensor receives the IR light, there is a high possibility of an unsuitable configuration due to the following reason. The wavelength band (for example, the wavelength band of 680 nm) of the excitation light used for fluorescence may be in the red light region, or mat red color components as the color component are present inside the living body.

According to endoscope 10 of the second exemplary embodiment, the sensor sensitivity of IR and blue color image sensor 330 is that of the high sensitivity sensor. Therefore, compared to the sensor sensitivity of the normal sensitivity sensor, IR and blue color image sensor 330 has a characteristic which is highly sensitive on the long wavelength in the IR light region. Accordingly, endoscope 10 can improve the spectral sensitivity of the IR light, compared to the spectral sensitivity of the RGB light in the visible light region.

As illustrated in FIG. 16, in the blue light region, the sensor sensitivity of the high sensitivity sensor is approximately the same as the sensor sensitivity of the normal sensitivity sensor. Therefore, even if the normal sensitivity sensor is replaced with the high sensitivity sensor, endoscope 10 can restrain the color balance from being disturbed in the visible light region.

In this way, in endoscope 10, the color separation prism may include three color separation prism 20A which separates the light incident from the object into three color components of the red color component, the green color component, and the blue color component and the infrared light component. The image sensor may include three image sensors 330 to 332 which respectively convert the optical image of the three separated color components into the electric signals.

In this manner, even in a case where three color separation prism 20A is used, endoscope 10 can improve the spectral sensitivity in the wavelength region of the infrared light, compared to the spectral sensitivity in the wavelength region of the three primary color light in the visible light region. Accordingly, for example, in a case where the affected area is imaged using the ICG, the fluorescing affected area is easily visible using the IR image by restraining a change in the RGB image showing the entire area including the affected area.

Endoscope 10 causes one image sensor to detect the blue color component and the infrared light component. In this manner, even if the high sensitivity sensor is used as the image sensor, endoscope 10 can improve the spectral sensitivity of the infrared light component by reducing a change in the spectral sensitivity of the blue color component. Therefore, visibility of the infrared light component can be improved by restraining poor color reproducibility (change in distribution of each color component) of each color component of three primary colors.

Third Exemplary Embodiment

The first exemplary embodiment employs the quadruple board-type prism, and the second exemplary embodiment employs the triple board-type prism. However, in a third exemplary embodiment, a case of employing a double board-type prism for separating the light into the IR light and the RGB, light will be described.

In the present exemplary embodiment, the same reference numerals will be given to the same matters as those in the first exemplary embodiment or the second exemplary embodiment, and description thereof will be omitted or simplified.

Figure 18:
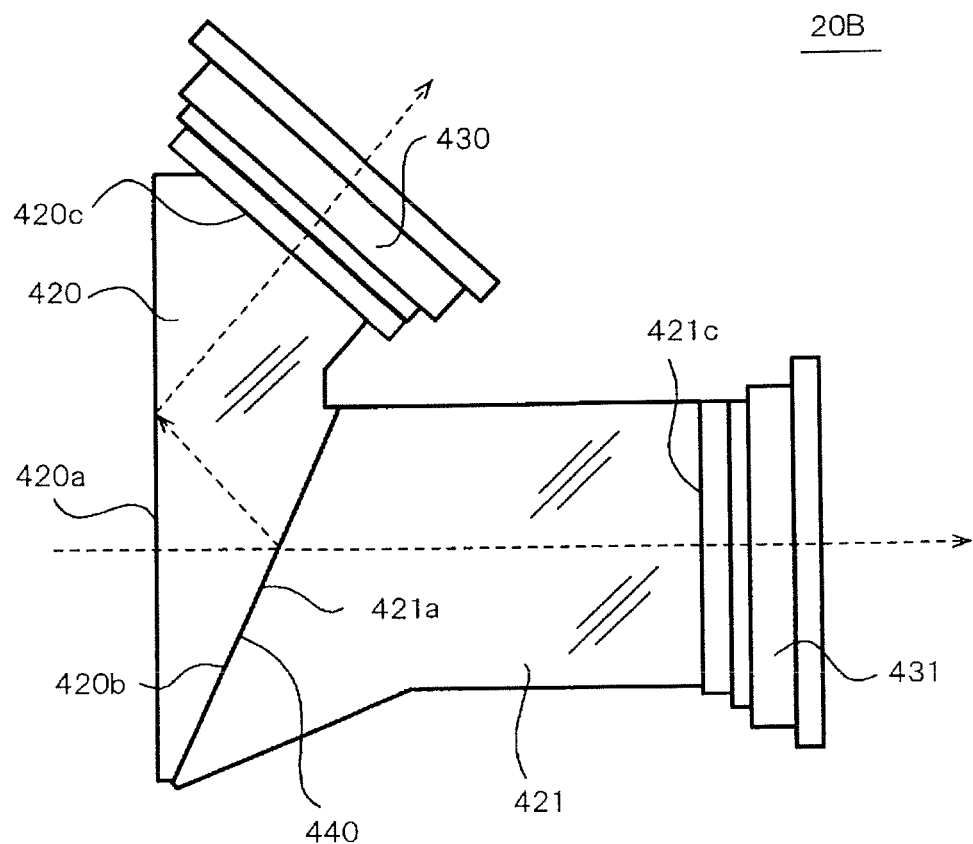
FIG. 18 is a view illustrating a structure example of a two color separation prism according to a third exemplary embodiment.

FIG. 18 is a view illustrating a structure example of two color separation prism 20B according to the third exemplary embodiment. Two color separation prism 20B separates the incident light guided by relay lens 13 into the light of the RGB component which is the light of the three primary color light, and the light of the IR component. In two color separation prism 20B, IR separation prism 420 and RGB color separation prism 421 are sequentially assembled in the optical axis direction.

IR image sensor 430 is disposed to face light emission surface 420c of IR separation prism 420. RGB color image sensor 431 is disposed to face light emission surface 421c of RGB color separation prism 421.

For example, image sensors 430 and 431 are CCD or CMOS image sensors including respective pixels which are arrayed in the horizontal (H) direction and the vertical (V) direction. Image sensors 430 and 431 convert the optical image in which the light separated into two colors of the IR and the RGB colors forms an image on each imaging surface, into the electric signal.

In IR separation prism 420, the incident light is incident on incident surface 420a of IR separation prism 420. The light reflected on reflective surface 420b facing incident surface 420a is totally reflected at a boundary of incident surface 420a of IR separation prism 420, and is incident on IR image sensor 430 after being emitted from light emission surface 420c facing incident surface 420a. For example, IR reflective film 440 is formed on reflective surface 420b by vapor deposition. IR separation prism 420 causes the IR light in the incident light to be reflected thereon, and causes other light (light of the RGB component) to be transmitted therethrough. IR image sensor 430 causes the light reflected on reflective surface 420b and incident surface 420a to be incident thereon, thereby receiving the light. In this way, IR separation prism 420 is molded so that the light moves forward in IR separation prism 420.

In RGB color separation prism 421, the light (incident light) transmitted through IR separation prism 420 is incident on incident surface 421a of RGB color separation prism 421, and is incident on RGB image sensor 431 after being emitted from light emission surface 421c facing incident surface 421a. In this way, RGB color separation prism 421 is molded so that the light moves forward in RGB color separation prism 421.

In the double board-type camera (two color separation prism 20B and image sensors 430 and 431), in a case of the C-mount, the optical distance (optical path length) from flange surface 13v of relay lens 13 to image sensors 430 and 431 is also set to 17.526 mm. The refractive index of two color separation prism 20B may be the same as "1.8" which is the refractive index of four color separation prism 20. In a case of the double board-type camera, there is more room in the layout space, compared to the quadruple board-type camera. Accordingly, the refractive index of two color separation prism 20B may be a smaller refractive index value than that of the quadruple board-type camera or the triple board-type camera, for example, "1.7" or smaller than "1.7". Compared to the quadruple board-type camera or the triple board-type camera, the refractive index has the smaller value. Accordingly, the actual distance (length) of the double board-type camera is shortened.

Figure 19:
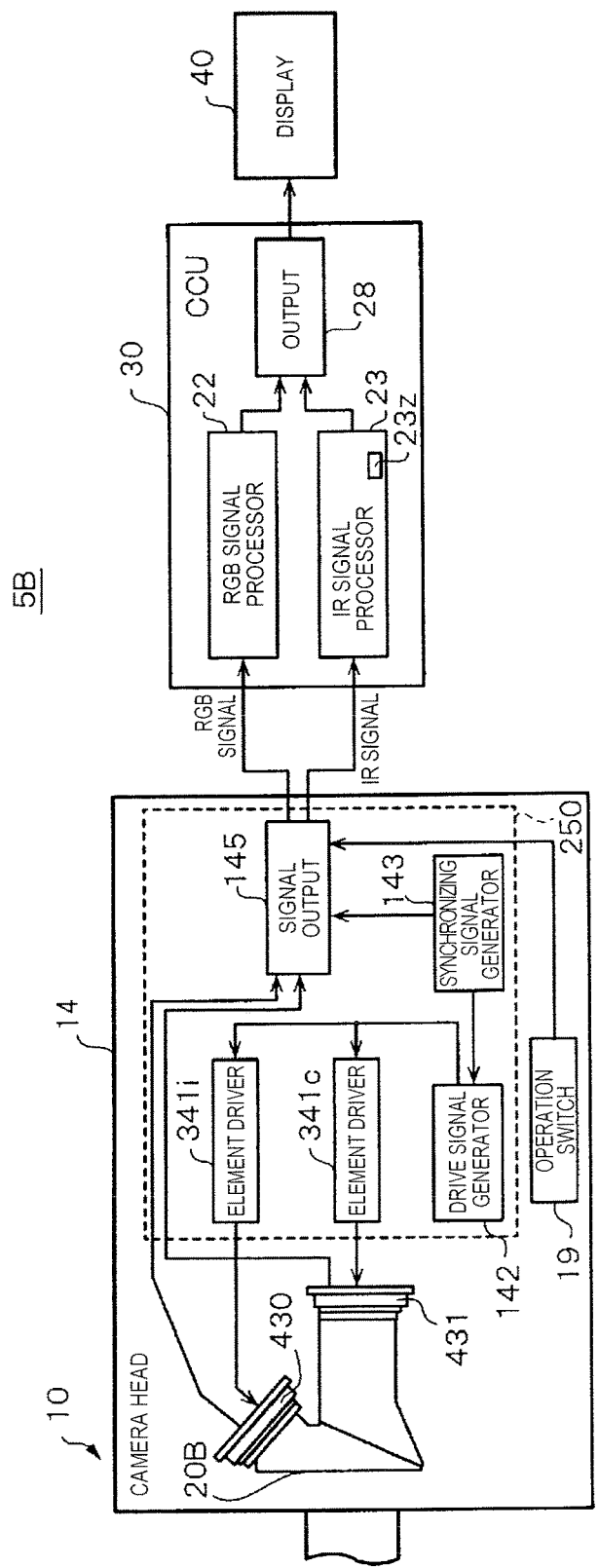
FIG. 19 is a block diagram illustrating a configuration example of an endoscope system according to the third exemplary embodiment.

FIG. 19 is a block diagram illustrating a configuration example of endoscope system 5B according to the third exemplary embodiment. The endoscope system according to the third exemplary embodiment has substantially the same configuration as that according to the first or second exemplary embodiment. The same reference numerals will be given to the same configuration elements as those according to the first or second exemplary embodiment, and description thereof will be omitted or simplified. Here, a configuration and an operation which are different from those according to the first or second exemplary embodiment will be described.

Unlike the first exemplary embodiment, according to the third exemplary embodiment, two element driver 341i and element driver 341c are mounted on electronic board 250.

Element driver 341*i* drives IR image sensor 430 in accordance with a drive signal. Element driver 341*c* drives RGB image sensor 431 in accordance with a drive signal.

Drive signal generator 142 generates the drive signals for each of element drivers 341*i* and 341*c*.

Signal output 145 transmits the electric signal output from image sensors 430 and 431 to CCU 30. A configuration and an operation of CCU 30 are the same as those according to the first exemplary embodiment, and CCU 30 processes the IR signal and the RGB signal.

Figure 20:
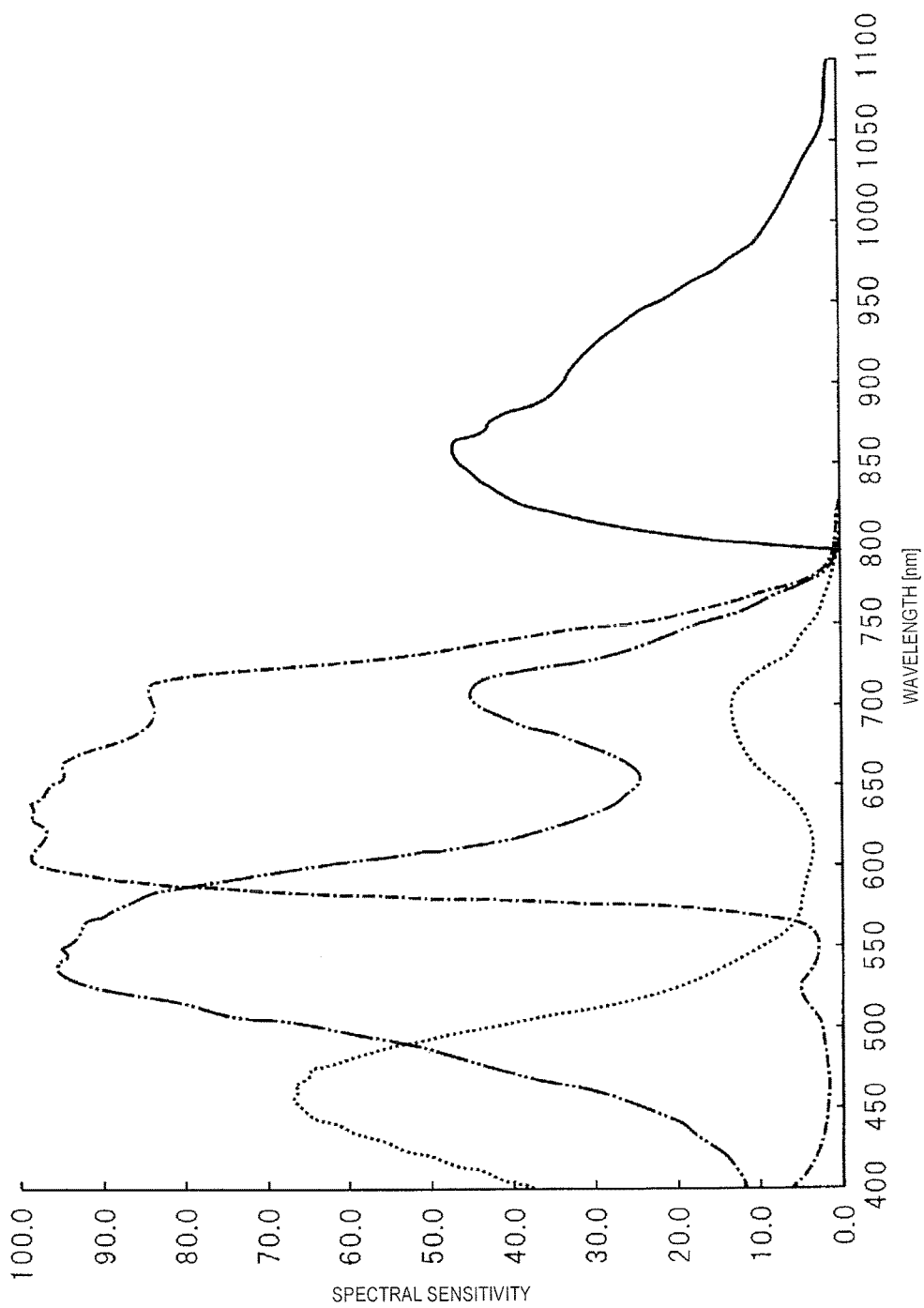
FIG. 20 is a graph illustrating spectral sensitivity in a case where two image sensors are used.
Figure 21:
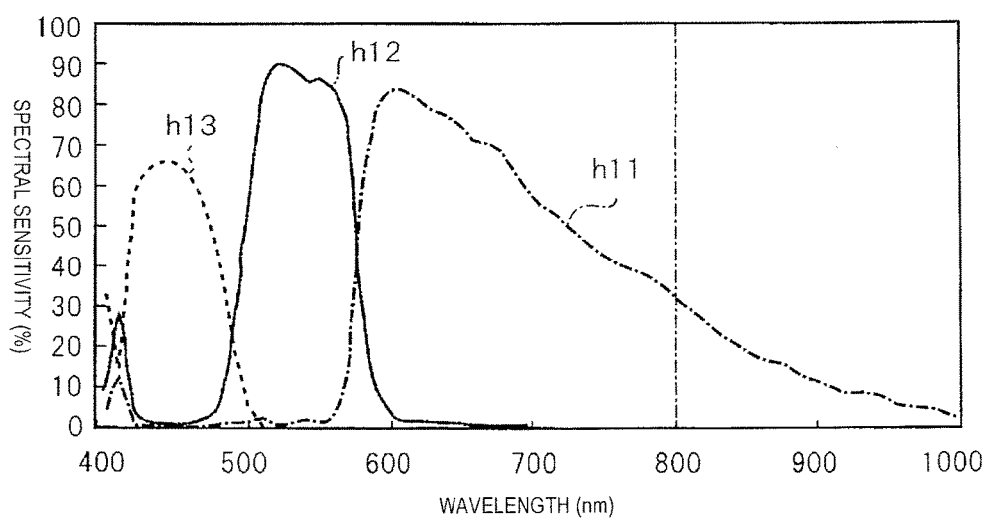
FIG. 21 is a graph illustrating spectral sensitivity of a three color separation prism according to the comparative example.

FIG. 20 is a graph illustrating spectral sensitivity in a case where two image sensors 430 and 431 are used. The vertical axis in FIG. 20 represents the spectral sensitivity in units of percentage. The horizontal axis in FIG. 20 represents a wavelength (nm) of the light incident on respective image sensors 430 and 431. The spectral sensitivity corresponds to the light quantity of the light having each wavelength detected by image sensors 430 and 431 with respect to the light quantity of the light incident on two color separation prism 20B. The spectral sensitivity is obtained in such a way that the sensor sensitivity illustrated in FIG. 6 is multiplied by the spectral transmittance of two color separation prism 20B. Although not illustrated, the spectral transmittance of two color separation prism 20B is the same as the spectral transmittance of three color separation prism 20A according to the second exemplary embodiment or the spectral transmittance of four color separation prism 20 according to the first exemplary embodiment, for example. The spectral sensitivity is one of performance indicators of the double board-type camera inside camera head 14.

IR image sensor 430 receives the IR light through IR separation prism 420. As IR image sensor 430, the high sensitivity sensor illustrated in the first exemplary embodiment is used. As RGB image sensor 431, the high sensitivity sensor may be used, or the normal sensitivity sensor may be used.

In the graph illustrated in FIG. 20, a peak value of the spectral sensitivity near the wavelength of 600 nm in the red light region is approximately 100%. On the other hand, a peak value of the spectral sensitivity near the wavelength of 860 nm in the IR region is approximately 47%. Therefore, the peak value of the spectral sensitivity in the IR region is approximately 47% (47%/100%) of the peak value of the spectral sensitivity of the wavelength of 600 nm, that is, 47% or greater. Therefore, the spectral sensitivity in the IR region is obtained so as to have a desired high value.

According to endoscope 10 of the third exemplary embodiment, the sensor sensitivity of IR light image sensor 430 is that of the high sensitivity sensor. Therefore, compared to the sensor sensitivity of the normal sensitivity sensor, IR and blue color image sensor 330 has a characteristic which is highly sensitive on the long wavelength in the IR light region. Accordingly, endoscope 10 can improve the spectral sensitivity of the IR light, compared to the spectral sensitivity of the RGB light in the visible light region.

Since the double board-type camera is used, compared to the quadruple board-type camera or the triple board-type camera, the layout space has more room, and thus, the actual length can be lengthened. Therefore, the refractive index of the prism can be lowered. In this case, it is possible to reduce the cost required for the prism in endoscope 10. In endoscope 10, a size of camera head 14 can be miniaturized by maintaining a state where the actual length of the double board-type camera is short.

In this way, in endoscope 10, the color separation prism may include two color separation prism 20B which separates the light incident from the object into two color components of the three primary color light and the infrared light. The image sensor may include two image sensors 430 and 431 which respectively convert the optical image of the two separated color components into the electric signals.

In this manner, even in a case where two color separation prism 20B is used, endoscope 10 can improve the spectral sensitivity in the wavelength region of the infrared light, compared to the spectral sensitivity in the wavelength region of the three primary color light in the visible light region. Accordingly, for example, in a case where the affected area is imaged using the ICG, the fluorescing affected area is easily visible using the IR image by restraining a change in the RGB image showing the entire area including the affected area.

Hitherto, various exemplary embodiments have been described with reference to the drawings. However, as a matter of course, the present invention is not limited by the examples. Those skilled in the art will appreciate that various modification examples or correction examples are conceivable within the scope described in claims. As a matter of course, it is obvious that those examples belong to the technical scope of the present invention.

For example, in the above-described exemplary embodiments, an example has been described in which a rigid endoscope is employed as endoscope 10. However, a rigid endoscope having another configuration may be employed, or a soft endoscope may be employed. The configuration or the operation of endoscope 10 may be applied to an optical microscope. Relay lens 13 and camera head 14 comply with the standards of the C-mount, thereby improving versatility. Accordingly, the above-described exemplary embodiments can be easily applied to the optical microscope.

In the above-described exemplary embodiments, an example has been described in which the ICG is administered into the living body as an optical contrast agent. However, any other optical contrast agent instead of the ICG may be administered. In this case, in accordance with the wavelength of the excitation light for exciting the optical contrast agent, the spectroscopic properties or the spectral sensitivity in the wavelength region of the invisible light may be determined.

In the above-described exemplary embodiments, a chemical which fluoresces in the wavelength region of the infrared light is used. However, a chemical which fluoresces in the wavelength region of ultraviolet light may be used. Even in this case, similarly to a case where the optical contrast agent which fluoresces in the near infrared light region, the endoscope can capture an image of the affected area which fluoresces.

In the above-described exemplary embodiments, an example has been mainly described in which relay lens 13 and camera head 14 comply with the standards of the C-mount. However, both of these may not comply with the standards of the C-mount.

In the above-described exemplary embodiments, a configuration of reference numeral 13 may be the mount adapter. Alternatively, configuration may be adopted in which the mount adapter internally has the relay lens.

In the above-described exemplary embodiments, CCU 30 has been described as an example of the processor. As long as the processor controls endoscope system 5, the processor may adopt any physical configuration. Therefore, the processor is not limited to CCU 30. However, if programmable CCU 30 is used, processing content can be changed by changing the program. Accordingly, the processor can be more freely designed. The processor may be configured to include one semiconductor chip, or may be configured to physically include a plurality of semiconductor chips. In a case where the processor is configured to include the plurality of semiconductor chips, each control in the first exemplary embodiment may be realized by each different semiconductor chip. In this case, it is conceivable that the plurality of semiconductor chips configure one processor. The processor may be configured to include a member (capacitor or the like) having a function which is different from that of the semiconductor chip. One semiconductor chip may be configured so as to realize a function belonging to the processor and other functions. As long as a programmable circuit is used, with regard to the circuit mounted on electronic board 250, the processing content can be changed by changing the program. The number of circuits may be one or more.

What is claimed is:

1. An endoscope comprising:
   a four color separation prism that includes a first color separation prism, a second color separation prism, a third color separation prism, and a fourth color separation prism which respectively separate light incident from an affected area into a first color component, a second color component, a third color component, and a fourth color component which are any one of a blue color component, a red color component, a green color component, and an IR component;
   a first color image sensor that is installed in the first color separation prism, and that converts the separated first color component into an electric signal;
   a second color image sensor that is installed in the second color separation prism, and that converts the separated second color component into an electric signal;
   a third color image sensor that is installed in the third color separation prism, and that converts the separated third color component into an electric signal;
   a fourth color image sensor that is installed in the fourth color separation prism, and that converts the separated fourth color component into an electric signal; and
   a signal output that outputs a color image signal and an IR signal from the respectively converted electric signals,
   wherein the first color separation prism, the second color separation prism, the third color separation prism, and the fourth color separation prism are sequentially disposed from an object side when receiving the light incident from the affected area,
   wherein the first color image sensor is disposed opposite to the second color image sensor and the third color image sensor across an incident ray which is incident vertically to an object side incident surface of the first color separation prism, and
   wherein a first angle formed between the object side incident surface of the first color separation prism and a reflective surface of the first color separation prism is greater than a second angle formed between the object side incident surface of the first color separation prism and a reflective surface of the second color separation prism.

2. The endoscope of claim 1,
   wherein the first color separation prism is an IR separation prism, and
   wherein the first color image sensor is an IR image sensor.

3. The endoscope of claim 2,
   wherein the second color separation prism is a blue color separation prism, and
   wherein the second color image sensor is a blue color image sensor.

4. The endoscope of claim 2,
   wherein the fourth color separation prism is a green color separation prism, and
   wherein the fourth color image sensor is a green color image sensor.

5. The endoscope of claim 1,
   wherein the four color separation prism, the first color image sensor, the second color image sensor, the third color image sensor, and the fourth color image sensor are accommodated in a camera head gripped by a user when in use.

6. An endoscope comprising:
   a four color separation prism that includes a blue color separation prism, a red color separation prism, and a green color separation prism which respectively separate light incident from an affected area into a blue color component, a red color component, and a green color component, and an IR separation prism which separates the light incident from the affected area into an IR component;
   a blue color image sensor that is installed in the blue color separation prism, and that converts the separated blue color component into an electric signal;
   a red color image sensor that is installed in the red color separation prism, and that converts the separated red color component into an electric signal;
   a green color image sensor that is installed in the green color separation prism, and that converts the separated green color component into an electric signal;
   an IR image sensor that is installed in the IR separation prism, and that converts the separated IR component into an electric signal; and
   a lens that focuses the light incident from the affected area onto an imaging surface of the respective image sensors,
   wherein the IR separation prism is located closer to an object side than the blue color separation prism, the red color separation prism, and the green color separation prism when receiving the light incident from the affected area, and allows light having the blue color component, the red color component, and the green color component to be transmitted therethrough, and
   wherein an optical distance from a flange surface of the lens to the imaging surface of the respective image sensors is 17.526 mm.

7. The endoscope of claim 6,
   wherein a maximum value of spectral sensitivity obtained by the IR separation prism and the IR image sensor is equal to or greater than 40% of a maximum value of the spectral sensitivity in a wavelength band of three primary color light.

8. The endoscope of claim 7,
   wherein in the IR image sensor, sensor sensitivity in a wavelength band of 830 nm is equal to or greater than 50% of sensor sensitivity in a wavelength band of 510 nm.

9. A four color separation endoscope prism comprising:
   a first color separation prism, a second color separation prism, a third color separation prism, and a fourth color separation prism which respectively separate light incident from an affected area into a first color component, a second color component, a third color component, and a fourth color component which are any one of a blue color component, a red color component, a green color component, and an IR component,
   wherein the first color separation prism, the second color separation prism, the third color separation prism, and the fourth color separation prism are sequentially disposed from an object side when receiving the light incident from the affected area, wherein a light emission surface of the first color separation prism is disposed opposite to a light emission surface of the second color separation prism and a light emission surface of the third color separation prism across an incident ray which is incident vertically to an object side incident surface of the first color separation prism, and wherein a first angle formed between the object side incident surface of the first color separation prism and a reflective surface of the first color separation prism is greater than a second angle formed between the object side incident surface of the first color separation prism and a reflective surface of the second color separation prism.

10. An image display method comprising:

separating, by a four color separation prism of an endoscope, light incident from an affected area into four color components, the four color separation prism including a first color separation prism, a second color separation prism, a third color separation prism, and a fourth color separation, and the four color components including a first color component, a second color component, a third color component, and a fourth color component which are any one of a blue color component, a red color component, a green color component, and an IR component;

converting, by a first color image sensor that is installed in the first color separation prism, the separated first color component into an electric signal;

converting, by a second color image sensor that is installed in the second color separation prism, the separated second color component into an electric signal;

converting, by a third color image sensor that is installed in the third color separation prism, the separated third color component into an electric signal;

converting, by a fourth color image sensor that is installed in the fourth color separation prism, the separated fourth color component into an electric signal; and outputting, by a signal output, a color image signal and an IR signal from the respectively converted electric signals, wherein the first color separation prism, the second color separation prism, the third color separation prism, and the fourth color separation prism are sequentially disposed from an object side when receiving the light incident from the affected area, wherein the first color image sensor is disposed opposite to the second color image sensor and the third color image sensor across an incident ray which is incident vertically to an object side incident surface of the first color separation prism, and wherein a first angle formed between the object side incident surface of the first color separation prism and a reflective surface of the first color separation prism is greater than a second angle formed between the object side incident surface of the first color separation prism and a reflective surface of the second color separation prism.

* * * * *